United States Patent
Zhang et al.

(10) Patent No.: US 12,131,824 B2
(45) Date of Patent: Oct. 29, 2024

(54) METHOD AND SYSTEM FOR CONTROLLING MEDICAL DEVICE FOR SWITCHING DISPLAY OF A TERMINAL TO A PRESET TARGET MODE

(71) Applicant: SHANGHAI UNITED IMAGING HEALTHCARE CO., LTD., Shanghai (CN)

(72) Inventors: Jianjun Zhang, Shanghai (CN); Wensong Chen, Shanghai (CN)

(73) Assignee: SHANGHAI UNITED IMAGING HEALTHCARE CO., LTD. (CN)

( * ) Notice: Subject to any disclaimer, the term of this patent is extended or adjusted under 35 U.S.C. 154(b) by 595 days.

(21) Appl. No.: 17/427,966

(22) PCT Filed: Dec. 2, 2019

(86) PCT No.: PCT/CN2019/122398
§ 371 (c)(1),
(2) Date: Aug. 3, 2021

(87) PCT Pub. No.: WO2020/119500
PCT Pub. Date: Jun. 18, 2020

(65) Prior Publication Data
US 2022/0101993 A1   Mar. 31, 2022

(30) Foreign Application Priority Data

Dec. 14, 2018 (CN) ......................... 201811532578.6
Aug. 5, 2019 (CN) ......................... 201910716688.6
Nov. 14, 2019 (CN) ......................... 201911111441.8

(51) Int. Cl.
G16H 40/20   (2018.01)
G16H 40/67   (2018.01)

(52) U.S. Cl.
CPC ............. G16H 40/67 (2018.01); G16H 40/20 (2018.01)

(58) Field of Classification Search
CPC .............................. Y10S 700/00; G16H 40/20
See application file for complete search history.

(56) References Cited

U.S. PATENT DOCUMENTS 8,092,426 B2    1/2012  Molnar
10,182,785 B2 *  1/2019  Daum ................... A61B 6/032
(Continued)

FOREIGN PATENT DOCUMENTS

CN          1861000 A     11/2006
CN        101589315 A     11/2009
(Continued)

OTHER PUBLICATIONS

International Search Report dated Mar. 3, 2020 issued in corresponding Patent Application No. PCT/CN2019/122398 w/English Translation (5 pages).
(Continued)

Primary Examiner — Suresh Suryawanshi
(74) Attorney, Agent, or Firm — Polsinelli PC

(57) ABSTRACT

The present disclosure relates to a method and system for controlling a medical device. The method includes: detecting, by an information detection apparatus, identification information of a terminal within a preset safety distance, and sending the identification information to the device control apparatus; determining, by the terminal, a current permission function of the terminal according to an acquired target operation parameter when the identification information passes verification of a device control apparatus; the target operation parameter including a target region where the terminal is currently located and a target safety condition; receiving, by the device control apparatus, an operation (Continued)

instruction corresponding to the permission function and sent by the terminal, and controlling the medical device to perform an operation corresponding to the operation instruction; and switching, by the terminal, a display mode to a preset target mode when a current state of the terminal satisfies a preset condition.

12 Claims, 11 Drawing Sheets

(56) References Cited

U.S. PATENT DOCUMENTS

| | | | |
|---|---|---|---|
| 2009/0069640 A1 | 3/2009 | Rietzel et al. | |
| 2014/0098932 A1 | 4/2014 | Profio et al. | |
| 2015/0338988 A1* | 11/2015 | Lee .................. | G06F 3/0488 |
| | | | 345/173 |
| 2016/0275246 A1* | 9/2016 | Okusawa ........... | A61B 1/00009 |
| 2018/0277241 A1 | 9/2018 | Hamlin et al. | |

FOREIGN PATENT DOCUMENTS

| | | | | |
|---|---|---|---|---|
| CN | 102375659 A | | 3/2012 | |
| CN | 102547488 A | | 7/2012 | |
| CN | 103377016 A | * | 10/2013 | |
| CN | 104238912 A | * | 12/2014 | |
| CN | 104679795 A | * | 6/2015 | ............. G06F 21/31 |
| CN | 105278366 A | | 1/2016 | |
| CN | 105389456 A | | 3/2016 | |
| CN | 105577662 A | | 5/2016 | |
| CN | 106137628 A | | 11/2016 | |
| CN | 106355684 A | | 1/2017 | |
| CN | 106896983 A | * | 6/2017 | ........... G06F 21/316 |
| CN | 107004063 A | | 8/2017 | |
| CN | 107661111 A | | 2/2018 | |
| CN | 108156328 A | | 6/2018 | |
| CN | 109036536 A | | 12/2018 | |
| CN | 109659021 A | | 4/2019 | |
| DE | 10 2014 222 015 A1 | | 6/2016 | |
| EP | 2 584 452 A1 | | 4/2013 | |
| JP | 2017-151584 A | | 8/2017 | |

OTHER PUBLICATIONS

Chinese Office Action dated Mar. 3, 2022 issued in corresponding Patent Application No. 201911111441.8 (11 pages).
European Search Report dated Jan. 5, 2022 issued in corresponding Patent Application No. 19896250.8 (13 pages).
Chinese Office Action dated Nov. 3, 2021 issued in corresponding Patent Application No. 201910716688.6 (10 pages).

* cited by examiner

Safety region 1 | Safety region 2 | Exit the safety region

| Safety condition | Bed-movement enabled | Scanning enabled |
|---|---|---|
| Hand-held | No | Yes |
| Placed in a bracket | No | No |
| Detached | No | No |

Safety region 3

| Safety condition | Bed-movement enabled | Scanning enabled |
|---|---|---|
| Hand-held | Yes | Yes |
| Placed in a bracket | Yes | No |
| Detached | No | No |

Exit the safety region

| Safety condition | Screen lock | Read-only view |
|---|---|---|
| Hand-held | No | Yes |
| Detached | Yes | Yes |

Figure 8b

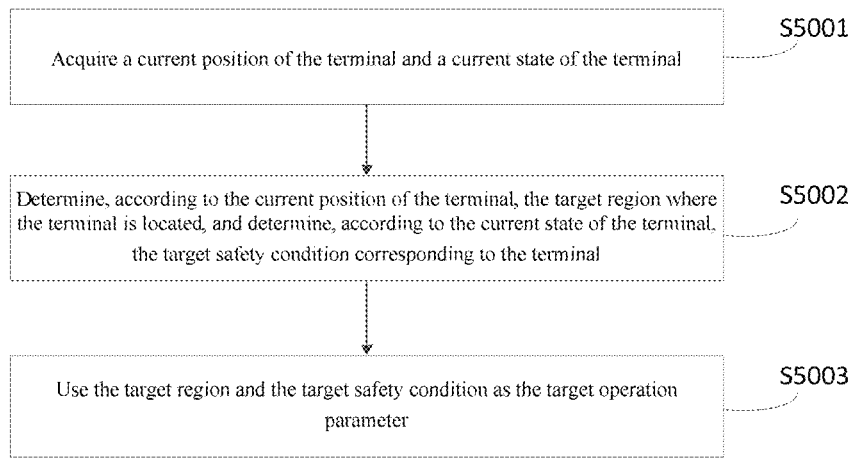

Figure 9

METHOD AND SYSTEM FOR CONTROLLING MEDICAL DEVICE FOR SWITCHING DISPLAY OF A TERMINAL TO A PRESET TARGET MODE

CROSS-REFERENCE TO RELATED APPLICATION

This application is a National Phase of International Application No. PCT/CN2019/122398, filed on Dec. 2, 2019 which claims priority to Chinese Patent Application No. 201811532578.6, filed on Dec. 14, 2018 and entitled "CONTROL METHOD AND CONTROL SYSTEM FOR MEDICAL DEVICE," Chinese Patent Application No. 201910716688.6, filed on Aug. 5, 2019 and entitled "DEVICE OPERATION METHOD, APPARATUS AND STORAGE MEDIUM," and Chinese Patent Application No. 201911111441.8, filed on Nov. 14, 2019 and entitled "TERMINAL MODE SWITCHING METHOD, APPARATUS, TERMINAL, SYSTEM AND READABLE STORAGE MEDIUM," all of which are incorporated herein by reference in their entireties.

TECHNICAL FIELD

The present disclosure relates to the field of medical device technologies, more particularly, to a method and system for controlling a medical device.

BACKGROUND

Sickbeds refer to beds used by patients for convalescing, including common and multi-functional sickbeds. The sickbeds may also be referred to as medical beds, nursing beds, etc. The sickbeds are used by patients for convalescing, and are mainly used in occasions such as major hospitals, township health centers, community health service centers and families.

With the progress of society and the development of science and technology, most sickbeds currently used in hospitals are controlled by an intelligent control device. Movement, fixation and the like of the sickbed can be controlled by a CPAN on a rack and/or a CTBOX in an operation room, or controlled by a wireless terminal. In order to facilitate a doctor to operate a medical device to scan a patient, a mobile terminal communicatively connected to the medical device has been added to assist the scanning of the medical device. The doctor can use the mobile terminal to control a position of the sickbed, and then return to a console of the medical device to control the medical device to scan the patient.

SUMMARY

Embodiments of the present disclosure provide a method for controlling a medical device, applied to a control system including an information detection apparatus, a device control apparatus and a terminal, the method including:

detecting, by the information detection apparatus, identification information of the terminal within a preset safety distance range, and sending the identification information to the device control apparatus;

determining, by the terminal, a current permission function of the terminal according to an acquired target operation parameter when the identification information has been verified the device control apparatus; the target operation parameter including a target region where the terminal is currently located and a target safety condition;

receiving, by the device control apparatus, an operation instruction corresponding to the permission function and sent by the terminal, and controlling the medical device to perform an operation corresponding to the operation instruction; and switching, by the terminal, a display mode to a preset target mode when a current state of the terminal satisfies a preset condition; the target mode being configured to display content to be displayed by the terminal.

In one embodiment, the method further includes:
matching, by the device control apparatus, the identification information with preset identification information for verification, the identification information passing the verification if the match is successful.

In one embodiment, the step of detecting, by the information detection apparatus, identification information of the terminal within a preset safety distance range includes:
detecting, by the information detection apparatus, identification information of at least one terminal within the preset safety distance range, the preset safety distance range being 0 m to 3 m.

In one embodiment, the step of matching, by the device control apparatus, the identification information with preset identification information for verification includes:
acquiring, by the device control apparatus, a plurality of identification information sent by the information detection apparatus; and
verifying the plurality of identification information and the preset identification information one by one.

In one embodiment, the step of determining, by the terminal, a current permission function of the terminal according to an acquired target operation parameter includes:
determining, by the terminal, the current permission function of the terminal according to the target operation parameter and a preset correspondence between operation parameters and permission functions.

In one embodiment, the step of determining, by the terminal, the current permission function of the terminal according to the target operation parameter and a preset correspondence between operation parameters and permission functions includes:
detecting, by the terminal, whether the target region belongs to a preset safety region, and detecting whether the target safety condition satisfies a preset safety condition, to obtain a detection result; and
determining, by the terminal, the current permission function of the terminal according to the detection result and the correspondence.

In one embodiment, the method further includes: detecting, by the terminal, the current state; and the step of detecting, by the terminal, the current state includes:
detecting, by the terminal, whether a preset sensing signal is received, or whether the terminal is in a charged state, or position information of the terminal.

In one embodiment, a current state of the terminal satisfying a preset condition includes:
determining that the current state of the terminal satisfies the preset condition if the terminal receives the sensing signal, the terminal is in a charged state, or the terminal is at a target position.

In one embodiment, the content to be displayed by the terminal is preset content stored in the terminal; and after the step of switching, by the terminal, a display mode to a preset target mode, the method further includes:

displaying the preset content in the target mode.

The embodiments of the present disclosure provide a system for controlling a medical device, the system including:

an information detection apparatus configured to detect identification information of the terminal within a preset safety distance range, and send the identification information to the device control apparatus;

a terminal configured to determine a current permission function of the terminal according to an acquired target operation parameter when the identification information has been verified the device control apparatus; the target operation parameter including a target region where the terminal is currently located and a target safety condition; and a device control apparatus configured to receive an operation instruction corresponding to the permission function sent by the terminal, and control the medical device to perform an operation corresponding to the operation instruction;

the terminal being further configured to switch a display mode to a preset target mode when a current state of the terminal satisfies a preset condition; the target mode being configured to display content to be displayed by the terminal.

In the method for controlling a medical device according to this embodiment, after the identification information of the terminal has been verified the device control apparatus, the terminal is used to send an operation instruction, and the operation instruction is sent under a current permission function of the terminal, which can thus greatly improve use safety of the terminal in the control over operation of the medical device and prevent potential safety hazards. In addition, the terminal may also be switched to a target operation mode when satisfying a particular condition, which greatly improves the utilization of the terminal and also improves interactivity of the terminal in use.

The embodiments of the present disclosure provide a method for controlling a medical device, applied to a control system including a detection apparatus and control apparatus, the method including:

detecting, by the detection apparatus, identification information of at least one terminal within a preset safety distance range;

acquiring, by the control apparatus, the identification information sent by the detection apparatus, and verifying the identification information; and receiving, by the control apparatus, an operation instruction corresponding to the identification information and currently sent by the terminal if a verification result is that the identification information is matched with preset identification information, and controlling, based on the operation instruction, the medical device to perform an operation corresponding to the operation instruction.

In one embodiment, the preset safety distance range is 0 m to 3 m.

In one embodiment, the step of acquiring, by the control apparatus, the identification information sent by the detection apparatus, and verifying the identification information includes:

acquiring, by the control apparatus, a plurality of identification information sent by the detection apparatus; and verifying the plurality of identification information and the preset identification information one by one.

In one embodiment, the step of detecting, by the detection apparatus, identification information of at least one terminal within a preset safety distance range includes:

detecting, by the detection apparatus, the identification information of the at least one terminal within the preset safety distance range in a preset cycle.

In one embodiment, prior to the step of receiving, by the control apparatus, an operation instruction corresponding to the identification information and currently sent by the terminal if a verification result is that the identification information is matched with preset identification information, and controlling, based on the operation instruction, the medical device to perform an operation corresponding to the operation instruction, the method further includes:

returning to the step of acquiring, by the control apparatus, identification information sent by the detection apparatus and verifying the identification information if the verification result is that the identification information is not matched with the preset identification information.

In one embodiment, the identification information is ID information of the terminal.

The embodiments of the present disclosure provide a control system, including:

a detection apparatus configured to detect identification information of at least one terminal within a preset safety distance range; and a control apparatus communicatively connected to the detection apparatus and the terminal and configured to obtain the identification information sent by the detection apparatus and verify the identification information, the control apparatus receiving an operation instruction corresponding to the identification information and sent by the terminal;

the control apparatus being further configured to control, based on the operation instruction, the medical device to perform an operation corresponding to the operation instruction; and the terminal being arranged between the detection apparatus and the medical device, and in use, the terminal being toward one side of the medical device.

In one embodiment, the detection apparatus further detects, based on a preset cycle, the identification information of the at least one terminal within the preset safety distance range.

In one embodiment, the detection apparatus includes:

a radio frequency identification card reader communicatively connected to the control apparatus and the at least one terminal and configured to detect the identification information of the at least one terminal within the preset safety distance range; and an emergency stop key adjacent to the radio frequency identification card reader and configured to control an emergency stop of the control system.

In one embodiment, the identification information is ID information of the terminal.

According to the method and system for controlling a medical device, the terminal can be detected within a safety distance range through the detection apparatus, and the control apparatus cooperates with the terminal to specifically operate the medical device. Potential safety hazards are prevented, so that a doctor can observe a patient while performing a specific operation on the medical device, so as to enable the doctor to control it more easily and conveniently, which is of higher safety.

The embodiments of the present disclosure provide a terminal operation method, including:

acquiring a target operation parameter of a terminal, the target operation parameter including a target region and a target safety condition;

determining a permission function corresponding to the target operation parameter according to a preset correspondence between operation parameters and permission functions; and enabling the permission function corresponding to the target operation parameter.

In one embodiment, the step of acquiring a target operation parameter of a terminal includes:

acquiring a current position of the terminal and a current state of the terminal;

determining, according to the current position of the terminal, the target region where the terminal is located, and determining, according to the current state of the terminal, the target safety condition corresponding to the terminal; and using the target region and the target safety condition as the target operation parameter.

In one embodiment, the step of determining a permission function corresponding to the target operation parameter according to a preset correspondence between operation parameters and permission functions includes:

detecting whether the target region belongs to a preset safety region, and detecting whether the target safety condition satisfies a preset safety condition, to obtain a detection result; and determining a permission function corresponding to the target region and the target safety condition according to the detection result and the correspondence.

In one embodiment, the step of determining a permission function corresponding to the target region and the target safety condition according to the detection result and the correspondence includes:

determining, according to the correspondence, that the permission function corresponding to the target region and the target safety condition is all functions of the terminal when the detection result is that the target region belongs to the preset safety region and the target safety condition satisfies the preset safety condition.

In one embodiment, the step of determining a permission function corresponding to the target region and the target safety condition according to the detection result and the correspondence includes:

disabling all the functions of the terminal when the detection result is that the target region does not belong to the preset safety region and the target safety condition does not satisfy the preset safety condition.

In one embodiment, the step of determining a permission function corresponding to the target region and the target safety condition according to the detection result and the correspondence includes:

determining, according to the correspondence, that the permission function corresponding to the target region is some functions of the terminal when the detection result is that the target region belongs to the preset safety region and the target safety condition does not satisfy the preset safety condition;

or determining, according to the correspondence, that the permission function corresponding to the target safety condition is some functions of the terminal when the detection result is that the target region does not belong to the preset safety region and the target safety condition satisfies the preset safety condition.

In one embodiment, the method further includes:

acquiring a user identification; and determining a user permission according to the user identification.

In one embodiment, the method further includes:

acquiring an operation level corresponding to the user identification when the user permission is satisfied;

acquiring a safety level function corresponding to the operation level according to a preset correspondence between operation levels and safety level functions; and enabling the safety level function corresponding to the operation level.

The embodiments of the present disclosure provide a terminal operation apparatus, including:

an acquisition module configured to acquire a target operation parameter of a terminal, the target operation parameter including a target region and a target safety condition;

a determination module configured to determine a permission function corresponding to the target operation parameter according to a preset correspondence between operation parameters and permission functions; and an enable module configured to enable the permission function corresponding to the target operation parameter.

The embodiments of the present disclosure provide a terminal including a memory and a processor, the memory storing a computer program, and the processor, when executing the computer program, performing the following steps:

acquiring a target operation parameter of a terminal, the target operation parameter including a target region and a target safety condition;

determining a permission function corresponding to the target operation parameter according to a preset correspondence between operation parameters and permission functions; and enabling the permission function corresponding to the target operation parameter.

The embodiments of the present disclosure provide a readable storage medium having a computer program stored thereon, the computer program, when executed by a processor, performing the following steps:

acquiring a target operation parameter of a terminal, the target operation parameter including a target region and a target safety condition;

determining a permission function corresponding to the target operation parameter according to a preset correspondence between operation parameters and permission functions; and enabling the permission function corresponding to the target operation parameter.

According to the terminal operation method, apparatus, terminal and storage medium, a target operation parameter of a terminal is acquired, the target operation parameter includes a target region and a target safety condition, a permission function corresponding to the target operation parameter is determined according to a preset correspondence between operation parameters and permission functions, and the permission function corresponding to the target operation parameter is enabled. In this embodiment, the enabled permission function is determined according to two parameters, i.e., the target region and the target safety condition, that is, different target regions and target safety conditions correspond to different permission functions; in this way, when a human body is examined, all the functions may not be blindly used for examination, and only the permission function corresponding to the target operation parameter is enabled. Therefore, the method can enhance safety of the terminal. At the same time, when a CT device is operated using the terminal, safety of the CT device may also be enhanced, thereby reducing occurrence of some unexpected risks.

The embodiments of the present disclosure provide a terminal mode switching method, including:

detecting a current state of a terminal; and switching a display mode of the terminal to a preset target mode if the current state of the terminal satisfies a preset condition; the target mode being configured to display content to be displayed by the terminal.

In one embodiment, the step of detecting a current state of a terminal includes:

detecting whether the terminal receives a preset sensing signal, or whether the terminal is in a charged state, or position information of the terminal.

In one embodiment, the step of detecting whether the terminal receives a preset sensing signal includes:

detecting whether the terminal receives a sensing signal sent by a sensor by near field communication.

In one embodiment, the current state of the terminal satisfying a preset condition includes:

determining that the current state of the terminal satisfies the preset condition if the terminal receives the sensing signal, the terminal is in a charged state, or the terminal is at a target position.

In one embodiment, the content to be displayed by the terminal is preset content stored in the terminal; and after the step of switching a display mode of the terminal to a preset target mode, the method further includes:

displaying the preset content in the target mode.

In one embodiment, the content to be displayed by the terminal is a display content sent by a control device; and after the step of switching a display mode of the terminal to a preset target mode, the method further includes:

receiving the display content sent by the control device; and displaying the display content sent by the control device in the target mode.

The embodiments of the present disclosure provide a terminal mode switching apparatus, including:

a detection module configured to detect a current state of a terminal; and a switching module configured to switch a display mode of the terminal to a preset target mode if the current state of the terminal satisfies a preset condition; the target mode being configured to display content to be displayed by the terminal.

The embodiments of the present disclosure provide a terminal including a memory, a processor and a display, the memory storing a computer program, and the processor, when executing the computer program, performing the following steps:

detecting a current state of the terminal; and switching a display mode of the terminal to a preset target mode if the current state of the terminal satisfies a preset condition; the target mode being configured to display content to be displayed by the terminal;

the display being configured to display content to be displayed by the terminal.

The embodiments of the present disclosure provide a terminal mode switching system, including a terminal and a control device, the terminal being communicatively connected to the control device; the terminal being configured to perform the following steps:

detecting a current state of the terminal; and switching a display mode of the terminal to a preset target mode if the current state of the terminal satisfies a preset condition; the target mode being configured to display content to be displayed by the terminal;

the control device being configured to send display content to the terminal.

The embodiments of the present disclosure provide a computer-readable storage medium having a computer program stored thereon, the computer program, when executed by a processor, performing the following steps:

detecting a current state of a terminal; and switching a display mode of the terminal to a preset target mode if the current state of the terminal satisfies a preset condition; the target mode being configured to display content to be displayed by the terminal.

According to the terminal mode switching method, apparatus, terminal, system and readable storage medium, a current state of the terminal can be detected; and a display mode of the terminal is switched to a preset target mode if the current state of the terminal satisfies a preset condition; the target mode being configured to display content to be displayed by the terminal. In the method, when a technician returns to an operation room with the terminal and no longer controls a sickbed, the terminal can automatically change the display mode to a target mode set as needed, which greatly improves the utilization of the terminal and also improves interactivity of the terminal in use.

BRIEF DESCRIPTION OF THE DRAWINGS

The accompanying drawings, which are incorporated herein and constitute a part of this specification, illustrate embodiments consistent with the present disclosure and, together with the specification, serve to explain principles of the present disclosure.

FIG. 8b is a schematic diagram of different operation parameters corresponding to different permission functions in the terminal operation method according to an embodiment;

FIG. 9 is a schematic flowchart of a terminal operation method according to another embodiment;

REFERENCE NUMERALS

100: information detection apparatus; 102: device control apparatus; 104: terminal; 20: control system;
200: detection apparatus; 202: control apparatus; 206: medical device; 2002: radio frequency identification card reader;
2004: emergency stop key; 602: control device.

DETAILED DESCRIPTION OF THE EMBODIMENTS

In order to make the objectives, technical solutions and advantages of the present disclosure clearer, the present disclosure is described in further detail below with reference to the accompanying drawings and embodiments. It should be understood that particular embodiments described herein are intended only to interpret the present disclosure and not intended to limit the present disclosure.

With the rapid development of medical imaging devices (also known as medical devices), an increasing number of people choose to use such medical devices for preliminary detection when various functions of the human body are detected, and then next detection or treatment is performed according to a preliminary detection result. In a current working process of a medical device, firstly, a patient enters a scanning room from a patients' access door, and then follows a technician's instructions to lie on a sickbed; the technician holds a terminal, operates the terminal to control the sickbed to rise and advance, and positions a to-be-scanned site of the patient; then, the technician returns to the operation room from a technicians' access door with the terminal, and operates a control device to complete examination on the patient; finally, the technician enters the scanning room from the technicians' access door with the terminal, tells the patient to go down the sickbed, and waits for next patient. The whole working process in the conventional art has problems of potential safety hazards caused by improper use of the terminal and low utilization of the terminal. A method and system for controlling a medical device according to embodiments of the present disclosure are intended to solve the above technical problems.

Figure 1:
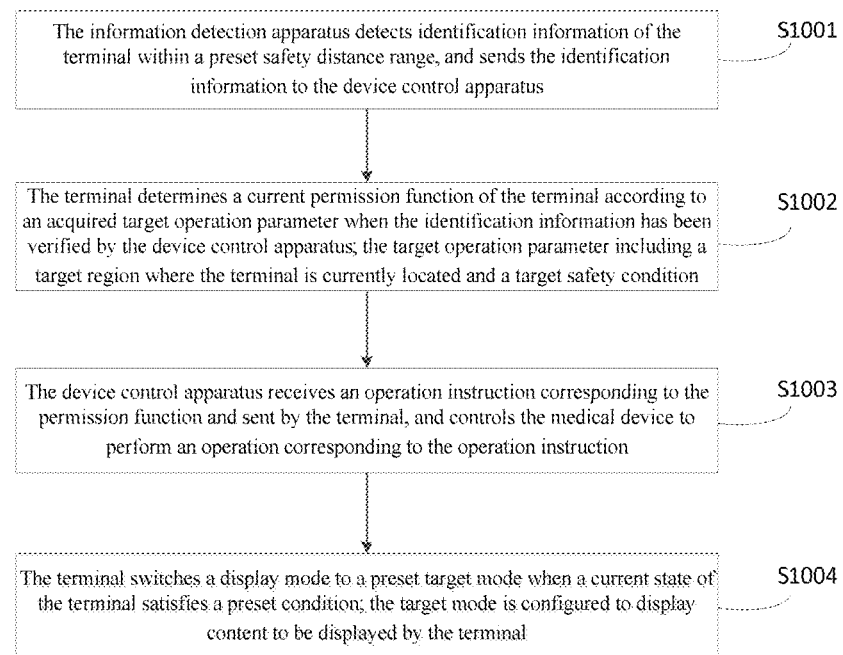
FIG. 1 is a schematic flowchart of a method for controlling a medical device according to an embodiment.

In one embodiment, as shown in FIG. 1, a method for controlling a medical device is provided. The method is applied to a control system including an information detection apparatus, a device control apparatus and a terminal. The method includes the following steps.

In S1001, the information detection apparatus detects identification information of the terminal within a preset safety distance range, and sends the identification information to the device control apparatus.

Specifically, a specific value of the preset safety distance range is not specifically limited in this embodiment, provided that safety of the terminal is ensured in use. Optionally, the preset safety distance range may be 1 m, 2 m or 3 m, which may be selected according to an actual requirement. The information detection apparatus may send the identification information to the device control apparatus after detecting the identification information of the terminal within the preset safety distance range. Optionally, the information detection apparatus and the device control apparatus may communicate with each other by wired data transmission or by wireless data communication.

Optionally, the information detection apparatus and the device control apparatus may be different hardware devices or integrated in a same hardware device. The hardware may be arranged on the medical device. The terminal may be a mobile terminal, and the identification information thereof is coded information or an ID number of the terminal.

In S1002, the terminal determines a current permission function of the terminal according to an acquired target operation parameter when the identification information has been verified by the device control apparatus; the target operation parameter including a target region where the terminal is currently located and a target safety condition.

Specifically, the device control apparatus, after receiving the identification information sent by the information detection apparatus, may verify the identification information to determine legality thereof. An operation instruction can be sent to the device control apparatus only when the identification information of the terminal is legal. Optionally, the device control apparatus may match the identification information with preset identification information to verify whether the identification information is legal, and the identification information passes verification if the match is successful. Optionally, when the process of the device control apparatus matching the identification information with preset identification information is a complete match, that is, when the identification information and the preset identification information are exactly the same, the match is considered to be successful. When the identification information has been verified by the device control apparatus, a signal indicative of successful verification may be sent to the terminal, and the terminal acquires its target operation parameter. The target operation parameter includes a target region where the terminal is currently located and a target safety condition. The target region is a region where the terminal is currently located. The target safety condition is a safety condition where the terminal is currently in.

Optionally, the terminal may determine the target region according to its current position, and determine the target safety condition according to its current state. The target region may be a safety region or a non-safety region. The safety region may include a scanning room and an operation room. The non-safety region may include other regions other than the scanning room and the operation room. The current state of the terminal may include any one of being held, detached, and placed in a bracket. The "held" means that the technician holds the terminal, the "placed in a bracket" means that the terminal is attached to a rack of the medical device or the terminal is placed in a bracket next to a control terminal, and the "detached" means that the terminal is neither held by the technician nor placed in the bracket, that is, placed elsewhere. The terminal may acquire a current position through a GPS positioning apparatus installed therein to determine the target region. The current state of the terminal is obtained according to a signal acquired by a human body sensor and whether a charging apparatus performs charging, to determine the target safety condition.

Then, the terminal determines a current permission function of the terminal according to the acquired target operation parameter. The terminal may first configure a correspondence among safety regions, safety conditions and permission functions; that is, different target regions correspond to different permission functions under different safety conditions. For example, when the terminal is in the safety region and in the hand-held state, a patient can be scanned and examined by using all functions. When the terminal is in the non-safety region and in the detached state, the terminal has no permission function.

In S1003, the device control apparatus receives an operation instruction corresponding to the permission function and sent by the terminal, and controls the medical device to perform an operation corresponding to the operation instruction.

Specifically, the terminal, after determining the current permission function, can send an operation instruction to the device control apparatus under the permission function. The device control apparatus, after receiving the operation instruction, can control the medical device to perform the operation corresponding to the operation instruction. For example, if the operation instruction sent by the terminal received by the device control apparatus is to move the sickbed forward, the sickbed is controlled correspondingly to move forward. Optionally, the terminal, when sending the operation instruction to the control terminal, is required to send it to the medical device to prevent potential safety hazards during operation.

In S1004, the terminal switches a display mode to a preset target mode when a current state of the terminal satisfies a preset condition; the target mode is configured to display content to be displayed by the terminal.

Specifically, after the device control apparatus fixes the bed position, the technician may take the terminal to return to the operation room for image scanning. In this case, the terminal may detect again whether its current state satisfies a preset condition. The preset condition may be a condition set for an operation state of the terminal or a condition set for a position state of the terminal. When the preset condition is the condition set for the position state of the terminal, if the terminal is in a state of being in the operation room, it is considered that the preset condition is satisfied, and the display mode of the terminal is switched to a target mode. When the preset condition is the condition set for the operation state of the terminal, if the operation state of the terminal is in a state of being in communication with the control device or in the charged state, it is considered that the preset condition is satisfied, and the display mode of the terminal is switched to the target mode. The control device may be a device that controls the medical device to scan the patient to obtain a medical image, that is, a control terminal operated by the technician.

The target mode may be a display operation mode preset according to a user requirement, which is set to, such as, display operation guidelines for operating the control device, display device parameters of the medical device, display physical sign information of the patient, or display content of a monitor in the scanning room. The target mode is configured to display content to be displayed by the terminal, but specific display content is not limited in this embodiment. Certainly, the target mode may also be configured to indicate other operation modes of the terminal, for example, a video recording mode, in which a process of the technician operating the control device currently is recorded for a new technician to learn.

After the terminal is switched to the target mode, a scanning process of the medical image may be extended from one screen of a conventional control device to two screens: one screen is an operation screen of the control device and the other screen is a display screen of the terminal, which provides more convenience for the technician to scan the medical image of the patient.

In the method for controlling a medical device according to this embodiment, after the identification information of the terminal has been verified the device control apparatus, the terminal is used to send an operation instruction, and the operation instruction is sent under a current permission function of the terminal, which can thus greatly improve use safety of the terminal in the control over operation of the medical device and prevent potential safety hazards. In addition, the terminal may also be switched to a target operation mode when satisfying a particular condition, which greatly improves the utilization of the terminal and also improves interactivity of the terminal in use.

Optionally, in some embodiments, the step of detecting, by the information detection apparatus, identification information of the terminal within a preset safety distance range includes: detecting, by the information detection apparatus, identification information of at least one terminal within the preset safety distance range, the preset safety distance range being 0 m to 3 m. That is, when a plurality of terminals are within the preset safety distance range, the information detection apparatus may detect a plurality of identification information and send the plurality of identification information to the device control apparatus. Optionally, the device control apparatus may acquire the plurality of identification information sent by the information detection apparatus and verify the plurality of identification information with the preset identification information one by one.

Optionally, in some embodiments, the step of determining, by the terminal, a current permission function of the terminal according to an acquired target operation parameter includes: determining, by the terminal, the current permission function of the terminal according to the target operation parameter and a preset correspondence between operation parameters and permission functions. Since the terminal is pre-configured with a correspondence between different operation parameters (including the safety region and the non-safety region) and different permission functions, the current permission function of the terminal can be determined according to the target operation parameter and the correspondence.

Figure 2:
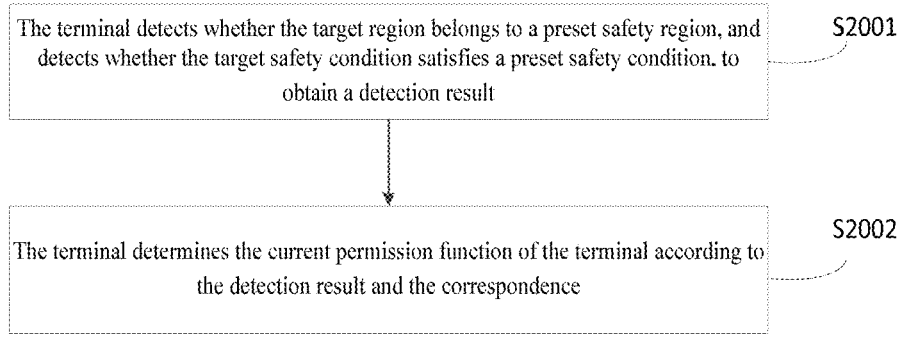
FIG. 2 is a schematic flowchart of a method for controlling a medical device according to another embodiment.

In one embodiment, as shown in FIG. 2, another method for controlling a medical device is provided. S1002 may include the following steps.

In S2001, the terminal detects whether the target region belongs to a preset safety region, and detects whether the target safety condition satisfies a preset safety condition, to obtain a detection result.

One or two or other numbers of preset safety regions may be provided. Two safety regions are provided in this embodiment, of which one is an operation room and the other is a scanning room. The safety region may be in a shape of a circle or a rectangle or other regular or irregular polygons.

Specifically, the terminal, after obtaining the target region and the target safety condition of the terminal, can detect whether the target region belongs to a preset safety region, to obtain the detection result; that is, the target region is matched with the preset safety region, if the match is successful, it indicates that the target region belongs to the preset safety region, and otherwise, it indicates that the region does not belong to the preset safety region but belongs to the non-safety region. In addition, the terminal may also detect whether the target safety condition satisfies the preset safety condition, to obtain the detection result; that is, the target safety condition may be matched with the preset safety condition, if the match is successful, it indicates that the target safety condition belongs to the preset safety condition, and otherwise, the target safety condition does not belong to the preset safety condition.

In S2002, the terminal determines the current permission function of the terminal according to the detection result and the correspondence.

Specifically, the terminal may obtain a plurality of detection results when detecting the target region and the target safety condition. The plurality of detection results may also correspond to a variety of different permission functions. The plurality of detection results may be as follows.

Optionally, it is determined, according to the correspondence, that the permission function corresponding to the target region and the target safety condition is all functions of the terminal when the detection result is that the target region belongs to the preset safety region and the target safety condition satisfies the preset safety condition. That is, the terminal can enable all the functions when detecting that the target region belongs to the preset safety region and the target safety condition satisfies the preset safety condition.

Optionally, all the functions of the terminal are disabled when the detection result is that the target region does not belong to the preset safety region and the target safety condition does not satisfy the preset safety condition. That is, when the terminal detects that the target region does not belong to the preset safety region and the target safety condition does not satisfy the preset safety condition, it is determined that the terminal may be in the non-safety region and in a non-safety state, and the terminal is required to disable all the functions.

Optionally, it is determined, according to the correspondence, that the permission function corresponding to the target region is some functions of the terminal when the detection result is that the target region belongs to the preset safety region and the target safety condition does not satisfy the preset safety condition; or it is determined, according to the correspondence, that the permission function corresponding to the target safety condition is some functions of the terminal when the detection result is that the target region does not belong to the preset safety region and the target safety condition satisfies the preset safety condition. In this step, some functions corresponding to the case of belonging to the safety region and not satisfying the safety condition and some functions corresponding to the case of not belonging to the safety region and satisfying the safety condition may be the same or different. The terminal may enable some functions when the obtained detection result is such two cases.

In the method for controlling a medical device according to this embodiment, a detection result is obtained by detecting whether the target region belongs to the preset safety region and detecting whether the target safety condition satisfies the preset safety condition, and a permission function corresponding to the target region and the target safety condition is determined according to the detection result and the correspondence. In this embodiment, permission functions corresponding to the terminal may also be different under different detection results; that is, permission functions used by the terminal in different scenarios are different. Therefore, the method can enhance the safety of the terminal in the process of controlling the medical device.

Optionally, in some embodiments, the method further includes: detecting, by the terminal, the current state; and the step of detecting, by the terminal, the current state includes: detecting, by the terminal, whether a preset sensing signal is received, or whether the terminal is in a charged state, or position information of the terminal. It is determined that the current state of the terminal satisfies the preset condition if the terminal receives the sensing signal, the terminal is in a charged state, or the terminal is at a target position. Optionally, the step of detecting, by the terminal, whether a preset sensing signal is received may include: detecting whether the terminal receives a sensing signal sent by a sensor by Near Field Communication (NFC). The sensor may be installed on the control device and may emit a sensing signal over a certain distance. A coverage range of the sensing signal is a regional range of the operation room. It may be determined, by detecting whether the terminal receives the sensing signal, that the terminal satisfies the preset condition. Optionally, a manner in which the terminal detects whether it is in the charged state may include: detecting whether a battery current of the terminal exceeds a current threshold, and determining that the terminal is in the charged state if yes. Optionally, the position information of the terminal may be obtained by a user input, obtained by identification of an image taken by a camera in the operation room, or by a signal from the GPS positioning apparatus in the terminal. It may be determined, by detecting whether the position of the terminal is in a region of the operation room (i.e., target position), that the terminal satisfies the preset condition.

Optionally, in some embodiments, the content to be displayed by the terminal is preset content stored in the terminal, for example, operation guidelines for operating the control device. The preset content is pre-stored in the terminal. After the terminal switches the display mode to the preset target mode, the preset content is automatically displayed in the target mode. Thus, power consumption of communication between the terminal and the control device is reduced, and the operation complexity of the terminal is reduced.

Optionally, in some embodiments, the content to be displayed by the terminal is a display content sent by a control device, for example, device parameters of the medical device or displayed physical sign information of a subject. The display content sent by the control device may be sent according to an input instruction of the technician; that is, the control device can send the display content to the terminal according to a user requirement.

It should be understood that although steps in the flowcharts of FIG. 1 and FIG. 2 are displayed in sequence as indicated by the arrows, the steps are not necessarily performed in sequence in the order indicated by the arrows. Unless otherwise clearly specified herein, the steps are performed without any strict sequence limitation, and may be performed in other orders. In addition, at least some steps in FIG. 1 and FIG. 2 may include a plurality of sub-steps or a plurality of stages, and these sub-steps or stages are not necessarily performed at a same moment, and may be performed at different moments. The sub-steps or stages are not necessarily performed in sequence, and the sub-steps or stages and at least some of other steps or sub-steps or stages of other steps may be performed in turn or alternately.

Figure 3:
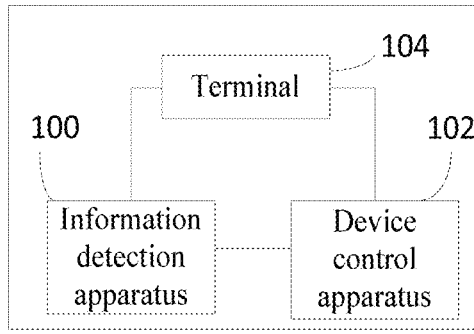
FIG. 3 is a schematic structural diagram of a system for controlling a medical device according to an embodiment.

In one embodiment, as shown in FIG. 3, a system for controlling a medical device is provided. The system includes an information detection apparatus 100, a device control apparatus 102 and a terminal 104.

Specifically, the information detection apparatus 100 is configured to detect identification information of the terminal 104 within a preset safety distance range, and send the identification information to the device control apparatus 102.

The terminal 104 is configured to determine a current permission function of the terminal 104 according to an acquired target operation parameter when the identification information has been verified by the device control apparatus 102. The target operation parameter includes a target region where the terminal 104 is currently located and a target safety condition.

The device control apparatus 102 is configured to receive an operation instruction corresponding to the permission function sent by the terminal 104, and control the medical device to perform an operation corresponding to the operation instruction.

The terminal 104 is further configured to switch a display mode to a preset target mode when a current state of the terminal 104 satisfies a preset condition. The target mode is configured to display content to be displayed by the terminal.

The implementation principle and technical effect of the system for controlling a medical device in this embodiment are similar to those in the above method embodiment, and are not described in detail herein.

In one embodiment, the device control apparatus 102 is specifically configured to match the identification information with preset identification information for verification. The identification information passes the verification if the match is successful.

In one embodiment, the information detection apparatus 100 is specifically configured to detect identification information of at least one terminal 104 within the preset safety distance range. The preset safety distance range is 0 m to 3 m.

In one embodiment, the device control apparatus 102 is specifically configured to acquire a plurality of identification information sent by the information detection apparatus 100; and verify the plurality of identification information and the preset identification information one by one.

In one embodiment, the terminal 104 is specifically configured to determine the current permission function of the terminal according to the target operation parameter and a preset correspondence between operation parameters and permission functions.

In one embodiment, the terminal 104 is specifically configured to detect whether the target region belongs to a preset safety region, and detects whether the target safety condition satisfies a preset safety condition, to obtain a detection result; and determine the current permission function of the terminal 104 according to the detection result and the correspondence.

In one embodiment, the terminal 104 is specifically configured to determine whether a preset sensing signal is received, or whether the terminal is in a charged state, or position information of the terminal 104.

In one embodiment, it is determined that the current state of the terminal 104 satisfies the preset condition if the terminal 104 receives the sensing signal, the terminal 104 is in the charged state, or the terminal 104 is at a target position.

In one embodiment, the content to be displayed by the terminal 104 is preset content stored in the terminal 104; and the terminal 104 is further configured to display the preset content in the target mode.

The above embodiments only describe several implementations of the present disclosure, which are described specifically and in detail, and therefore cannot be construed as a limitation on the patent scope of the present disclosure. It should be pointed out that those of ordinary skill in the art may also make several changes and improvements without departing from the ideas of the present disclosure, all of which fall within the protection scope of the present disclosure. Therefore, the patent protection scope of the present disclosure shall be subject to the appended claims.

Sickbeds refer to beds used by patients for convalescing, including common and multi-functional sickbeds. The sickbeds may also be referred to as medical beds, nursing beds, etc. The sickbeds are used by patients for convalescing, and are mainly used in occasions such as major hospitals, township health centers, community health service centers and families.

With the progress of society and the development of science and technology, most sickbeds currently used at the site of hospitals are controlled by an intelligent control device. Movement, fixation and the like of the sickbed can be controlled by a CPAN on a rack and/or a CTBOX in the operation room, or controlled by a wireless hand-held terminal.

Currently, when the wireless hand-held terminal is used in conjunction with an intelligent control device to move and fix the sickbed, there exist certain potential safety hazards, such as delay of a control signal of the hand-held terminal and invalid control of the hand-held terminal.

Based on this, there is a need to provide a method and system for controlling a medical device with respect to the problem of existence of certain potential safety hazards during the control of an existing hand-held terminal over the sickbed.

Figure 4:
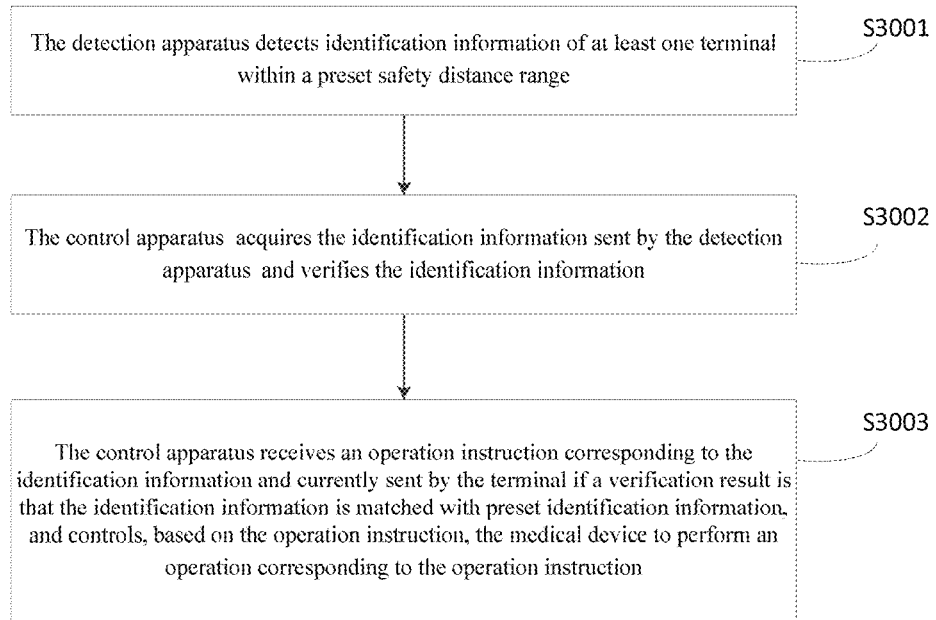
FIG. 4 is a schematic flowchart of a method for controlling a medical device according to an embodiment.
Figure 5:
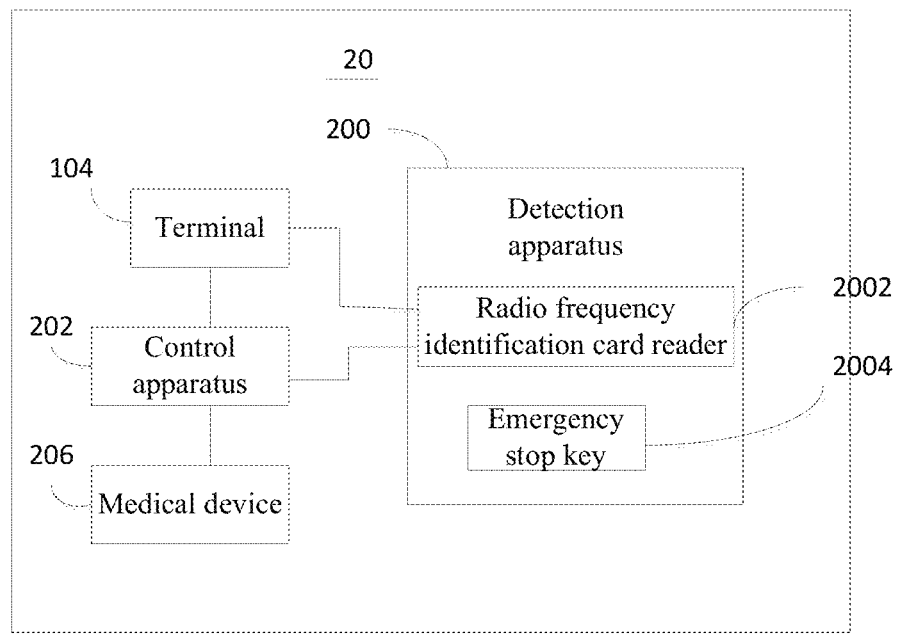
FIG. 5 is a structural block diagram of a control system according to an embodiment.

Referring to FIG. 4 and FIG. 5, an embodiment of the present disclosure provides a method for controlling a medical device, applied to a control system 20 including a detection apparatus 200 and control apparatus 202. The method includes the following steps.

In S3001, the detection apparatus 200 detects identification information of at least one terminal 104 within a preset safety distance range.

It may be understood that a specific value of the preset safety distance range is not specifically limited, provided that no potential safety hazards exist in use of the terminal 104. In one embodiment, the preset safety distance range may be set to 1 m. In one embodiment, the preset safety distance range may be set to 2 m. In one embodiment, the preset safety distance range may be set to 3 m. The specific value of the preset safety distance range may be selected according to an actual requirement.

In one embodiment, the detection apparatus 200 may detect the identification information of the terminal 104 only when the terminal 104 is within a safety detection distance range of the detection apparatus 200. In one embodiment, the identification information may be coded information of the terminal 104. In one embodiment, the identification information may also be an ID number.

In S3002, the control apparatus 202 acquires the identification information sent by the detection apparatus 200 and verifies the identification information.

It may be understood that a manner in which the control apparatus 202 acquires the identification information sent by the detection apparatus 200 is not limited, provided that the control apparatus 202 can acquire the identification information sent by the detection apparatus 200. In one embodiment, the control apparatus 202 may acquire the identification information sent by the detection apparatus 200 by wired data transmission. In one embodiment, the control apparatus 202 may also acquire the identification information sent by the detection apparatus 200 by wireless data transmission. In one embodiment, the wireless data transmission may be radio frequency signal transmission, Bluetooth signal transmission, or the like.

In one embodiment, a plurality of the identification information sent by the detection apparatus 200 is not limited. One or more pieces of identification information may be provided. In one embodiment, a plurality of identification information of the terminal 104 detected by the detection apparatus 200 within the preset safety distance range may be sent to the control apparatus 202 at the same time. Thus, the control apparatus 202 verifies the plurality of identification information one by one.

In S3003, the control apparatus 202 receives an operation instruction corresponding to the identification information and currently sent by the terminal 104 if a verification result is that the identification information is matched with preset identification information, and controls, based on the operation instruction, the medical device 206 to perform an operation corresponding to the operation instruction.

In one embodiment, "if a verification result is that the identification information is matched with preset identification information" means that the identification information is exactly the same as the preset identification information. The control apparatus 202 may determine that an identity of the current terminal 104 corresponding to the identification information is legal only when the identification information is exactly the same as the preset identification information. In one embodiment, if the identity of the current terminal 104 is legal, the control apparatus 202 receives an operation instruction sent by the current terminal 104, and generates a control command based on the operation instruction, so that the control apparatus 202 controls, based on the control command, the medical device 206 to perform an operation corresponding to the control command. In one embodiment, the medical device 206 may be a sickbed. In one embodiment, the operation may be sickbed movement, exposure, sickbed scanning and so on.

In one embodiment, in use, the terminal 104 is required to be operated toward the medical device 206 to prevent potential safety hazards during operation and improve safety. In one embodiment, the terminal 104 is required to be used between the medical device 206 and the detection apparatus 200.

In one embodiment, the detection apparatus 200 is communicatively connected to the control apparatus 202 and the terminal 104. In one embodiment, the control apparatus 202 is communicatively connected to the medical device 206.

In this embodiment, the terminal 104 can be detected within a safety distance range through the detection apparatus 200, and the control apparatus 202 cooperates with the terminal 104 to specifically operate the medical device 206. Potential safety hazards are prevented, so that a doctor can observe a patient while performing a specific operation on the medical device, to thereby enabling the doctor to control it more easily and conveniently, which is of higher safety.

In one embodiment, the preset safety distance range is 0 m to 3 m. In one embodiment, the detection apparatus 200 may detect the identification information of the terminal 104 only when the terminal 104 is within a safety detection distance range of the detection apparatus 200 (i.e., within 3 m around the detection apparatus 200). In one embodiment, one side of the detection apparatus 200 facing the medical device 206 may be set as a safety detection range, and one side of the detection apparatus 200 facing away from the medical device 206 may be set as a non-detection range.

In one embodiment, it may also be determined, by a camera according to a preset video algorithm, whether there is a person (whether there is a person can be determined by capturing a feature point of the person, such as head and shoulder, etc.) nearby an emergency stop button (arranged in the detection apparatus 200). If yes, an operation related to safety of a mobile terminal is allowed, and an operation direction of an operator is determined according to a handheld mode of the terminal 104 operated by the person. In one embodiment, sickbed movement can be normally performed if the sickbed movement is performed toward the sickbed, and the sickbed movement is not allowed if no. The safety may be further improved through cooperation between the camera and the detection apparatus 200.

In one embodiment, the step of acquiring, by the control apparatus 202, the identification information sent by the detection apparatus 200, and verifying the identification information includes: acquiring, by the control apparatus 202, a plurality of identification information sent by the detection apparatus 200; and verifying the plurality of identification information and the preset identification information one by one.

In one embodiment, the control apparatus 202 is in one-to-one correspondence to the preset identification information. That is, one control apparatus 202 can only match one terminal 104. In one embodiment, the control apparatus 202, when receiving a plurality of identification information, may verify the plurality of identification information one by one, and may stop verifying other pieces of identification information until a verification result is that the identification information is matched with the preset identification information. The safety in use is improved through such verification.

In one embodiment, the step of detecting, by the detection apparatus 200, identification information of at least one terminal 104 within a preset safety distance range includes: detecting, by the detection apparatus 200, the identification information of the at least one terminal 104 within the preset safety distance range in a preset cycle.

It may be understood that specific time of the preset cycle is not limited, provided that the detection apparatus 200 detects the identification information of the at least one terminal 104 within the preset safety distance range. In one embodiment, the preset cycle may be set to 200 ms (milliseconds). In one embodiment, the preset cycle may be set to 100 ms (milliseconds). The specific time of the preset cycle may be set according to an actual requirement.

In one embodiment, prior to the step of receiving, by the control apparatus 202, an operation instruction corresponding to the identification information and currently sent by the terminal 104 if a verification result is that the identification information is matched with preset identification information, and controlling, based on the operation instruction, the medical device 206 to perform an operation corresponding to the operation instruction, the method further includes:

returning to the step of acquiring, by the control apparatus 202, identification information sent by the detection apparatus 200 and verifying the identification information if the verification result is that the identification information is not matched with the preset identification information.

In one embodiment, when the verification result is that the identification information is not matched with the preset identification information, the control apparatus 202 re-acquires the identification information sent by the detection apparatus 200, and the detection apparatus 200 may stop verifying the identification information until the verification result is that the identification information is matched with the preset identification information. This improves the safety of the match between the control apparatus 202 and the terminal 104.

In one embodiment, the identification information is ID information of the terminal 104. In one embodiment, the ID information may be an identity number, a unique code, an exclusive number, and so on. In one embodiment, each terminal 104 corresponds to one piece of ID information.

Referring to FIG. 5, an embodiment of the present disclosure provides a control system 20 including a detection apparatus 200 and control apparatus 202. The detection apparatus 200 is configured to detect identification information of at least one terminal 104 within a preset safety distance range. The detection apparatus 202 is communicatively connected to the control apparatus 200 and the terminal 104. The control apparatus 202 is configured to acquire the identification information sent by the detection apparatus 200 and verify the identification information. The control apparatus 202 receives an operation instruction corresponding to the identification information and sent by the terminal 104 if a verification result is that the identification information is matched with preset identification information.

The control apparatus 202 is further configured to control, based on the operation instruction, the medical device 206 to perform an operation corresponding to the operation instruction. The terminal 104 is arranged between the detection apparatus 200 and the medical device 206, and in use, the terminal 104 is toward one side of the medical device 206.

It may be understood that a specific structure of the detection apparatus 200 is not limited, provided that the identification information of the at least one terminal 104 can be detected within the preset safety distance range. In one embodiment, the detection apparatus 200 may be an identification information card reader. The detection apparatus 200 may also be other chips with an identification information detection function.

It may be understood that a specific value of the preset safety distance range is not specifically limited, provided that no potential safety hazards exist in use of the terminal 104. In one embodiment, the preset safety distance range may be set to 1 m. In one embodiment, the preset safety distance range may be set to 2 m. In one embodiment, the preset safety distance range may be set to 3 m. The specific value of the preset safety distance range may be selected according to an actual requirement.

In one embodiment, the detection apparatus 200 may detect the identification information of the terminal 104 only when the terminal 104 is within a safety detection distance range of the detection apparatus 200. In one embodiment, the identification information may be coded information of the terminal 104. In one embodiment, the identification information may also be an ID number.

It may be understood that a specific structure of the control apparatus 202 is not limited, provided that the control apparatus 202 has a function of verifying the identification information and a function of controlling the medical device 206 (in one embodiment, the medical device 206 may be a sickbed). In one embodiment, the control apparatus 202 may be composed of a single-chip microprocessor and a display. In one embodiment, the control apparatus 202 may also be composed of a CPU (central processing unit) and a display.

It may be understood that a manner in which the control apparatus 202 acquires the identification information sent by the detection apparatus 200 is not limited, provided that the control apparatus 202 can acquire the identification information sent by the detection apparatus 200. In one embodiment, the control apparatus 202 may acquire the identification information sent by the detection apparatus 200 by wired data transmission. In one embodiment, the control apparatus 202 may also acquire the identification information sent by the detection apparatus 200 by wireless data transmission. In one embodiment, the wireless data transmission may be radio frequency signal transmission, Bluetooth signal transmission, or the like.

In one embodiment, a plurality of the identification information sent by the detection apparatus 200 is not limited. One or more pieces of identification information may be provided. In one embodiment, a plurality of identification information of the terminal 104 detected by the detection apparatus 200 within the preset safety distance range may be sent to the control apparatus 202 at the same time. Thus, the control apparatus 202 verifies the plurality of identification information one by one.

In one embodiment, "if a verification result is that the identification information is matched with preset identification information" means that the identification information is exactly the same as the preset identification information. The control apparatus 202 may determine that an identity of the current terminal 104 corresponding to the identification information is legal only when the identification information is exactly the same as the preset identification information. In one embodiment, if the identity of the current terminal 104 is legal, the control apparatus 202 receives an operation instruction sent by the current terminal 104, and generates a control command based on the operation instruction, so that the control apparatus 202 controls, based on the control command, the medical device 206 to perform an operation corresponding to the control command. In one embodiment, the operation may be sickbed movement, exposure, scanning of the medical device 206 and so on.

In one embodiment, in use, the terminal 104 is required to be operated toward the medical device 206 to prevent potential safety hazards during operation and improve safety. In one embodiment, the terminal 104 is required to be used between the medical device 206 and the detection apparatus 200.

In this embodiment, the terminal 104 can be detected within a safety distance range through the detection apparatus 200, and the control apparatus 202 cooperates with the terminal 104 to specifically operate the medical device 206. Potential safety hazards are prevented, so that a doctor can observe a patient while performing a specific operation on the medical device, to thereby enabling the doctor to control it more easily and conveniently, which is of higher safety.

In one embodiment, the detection apparatus 200 further detects, based on a preset cycle, the identification information of the at least one terminal 104 within the preset safety distance range. It may be understood that specific time of the preset cycle is not limited, provided that the detection apparatus 200 detects the identification information of the at least one terminal 104 within the preset safety distance range. In one embodiment, the preset cycle may be set to 200 ms (milliseconds). In one embodiment, the preset cycle may be set to 100 ms (milliseconds). The specific time of the preset cycle may be set according to an actual requirement.

In one embodiment, the detection apparatus 200 includes a radio frequency identification card reader 2002 and an emergency stop key 2004. The radio frequency identification card reader 2002 is communicatively connected to the control apparatus 202 and at least one terminal 104. The radio frequency identification card reader 2002 is configured to detect identification information of the at least one terminal 104 within the preset safety distance range. The emergency stop key 2004 is arranged adjacent to the radio frequency identification card reader 2002. The emergency stop key 2004 is configured to control an emergency stop of the control system 20.

In one embodiment, the radio frequency identification card reader 2002 and the control apparatus 202 may be communicatively connected by wireless data communication. In one embodiment, the radio frequency identification card reader 2002 and the at least one terminal 104 may be communicatively connected in the manner described in the above embodiment. Signal transmission may be more secure and stable by using an RFID (Radio Frequency Identification) technology. In one embodiment, when an emergency (such as a device failure) occurs in the control system 20, an emergency stop of the control system 20 can be controlled through the emergency stop key 2004.

In one embodiment, the preset safety distance range is 0 m to 3 m. In one embodiment, the detection apparatus 200 may detect the identification information of the terminal 104 only when the terminal 104 is within a safety detection distance range of the detection apparatus 200 (i.e., within 3 m around the detection apparatus 200). In one embodiment, one side of the detection apparatus 200 facing the medical device 206 may be set as a safety detection range, and one side of the detection apparatus 200 facing away from the medical device 206 may be set as a non-detection range.

In one embodiment, the identification information is ID information of the terminal 104. In one embodiment, the ID information may be an identity number, a unique code, an exclusive number, and so on. In one embodiment, each terminal 104 corresponds to one piece of ID information.

Based on the above, in the present disclosure, the terminal 104 can be detected within a safety distance range through the detection apparatus 200, and the control apparatus 202 cooperates with the terminal 104 to specifically operate the medical device 206. Potential safety hazards are prevented, so that a doctor can observe a patient while performing a specific operation on the medical device, to thereby enabling the doctor to control it more easily and conveniently, which is of higher safety.

The technical features in the above embodiments may be randomly combined. For concise description, not all possible combinations of the technical features in the above embodiments are described. However, all the combinations of the technical features are to be considered as falling within the scope described in this specification provided that they do not conflict with each other.

The above embodiments only describe several implementations of the present disclosure, which are described specifically and in detail, and therefore cannot be construed as a limitation on the invention patent scope. It should be pointed out that those of ordinary skill in the art may also make several changes and improvements without departing from the ideas of the present disclosure, all of which fall within the protection scope of the present disclosure. Therefore, the patent protection scope of the present disclosure shall be subject to the appended claims.

With the rapid development of medical imaging devices (also known as medical devices), an increasing number of people choose to use such medical devices for preliminary detection when various functions of the human body are detected, and then next detection or treatment is performed according to a preliminary detection result.

When a human body is detected using a medical device, in general, firstly, a patient lies on a sickbed, and through a mobile terminal, a doctor operates a position of the sickbed and positions a to-be-scanned site; then, the doctor uses the mobile terminal to control a device to scan the patient and controls a computer through the mobile terminal to process data scanned by the device and to display scanned data and scanned images at the same time. However, the above method has the problem of low safety.

Based on this, there is a need to provide a terminal operation method, apparatus and storage medium capable of improving the safety with respect to the above technical problem.

Figure 6:
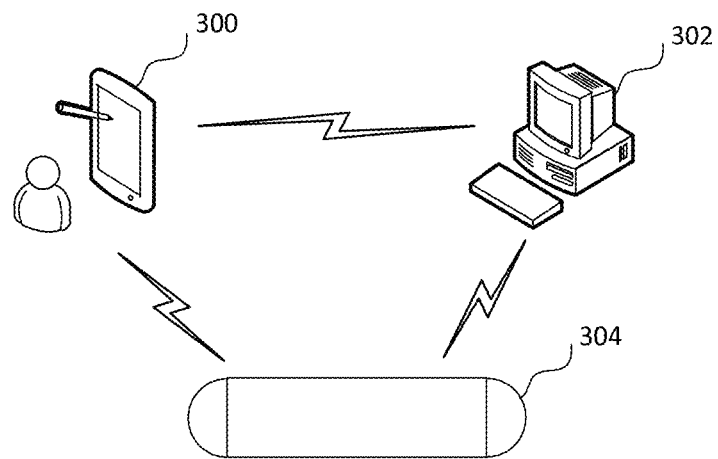
FIG. 6 is a diagram of an application environment of a terminal operation method according to an embodiment.

The device operation method according to the present disclosure can be applied to an application environment shown in FIG. 6. A mobile terminal 300 may communicate with a control terminal 302 or with a device 304. The control terminal 302 may also communicate with the device 304. Further, the mobile terminal 300 and the device 304 may be in a wireless connection or a wired connection. In the embodiment of the present disclosure, the device 304 is provided with a WIFI routing component, and the mobile terminal 300 may communicate with the device 304 by WIFI connection. The control terminal 302 and the device 304 may be in a wireless connection or a wired connection. In the embodiment of the present disclosure, the control terminal 302 and the device 304 are in a wired connection through a cable. the mobile terminal 300 and the control terminal 302 may be in a wireless connection or a wired connection. The mobile terminal 300, the control terminal 302 and the device 304 are generally in a same local area network. In addition, the mobile terminal 300 may be a mobile phone, a tablet computer, a hand-held computer and other mobile electronic products. The control terminal 302 may be a personal laptop computer, a desktop computer, or the like. The device 304 may be a CT device or the like.

Figure 7:
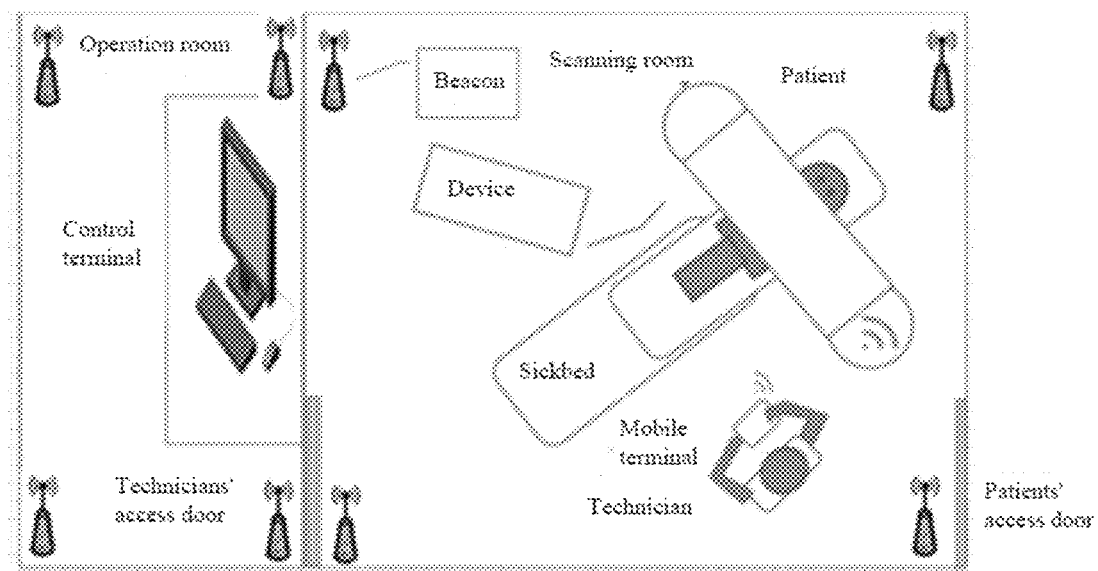
FIG. 7 is a schematic diagram of a process of human body examination according to an embodiment.

Referring to FIG. 7, in the embodiment of the present disclosure, a process of scanning the patient may be as follows: firstly, a patient enters a scanning room from a patients' access door, and then follows a technician's instructions to lie on a sickbed; the technician holds the mobile terminal, operates the mobile terminal to control the sickbed to rise and advance, and positions a to-be-scanned site of the patient; then, the technician returns to the operation room from a technicians' access door with the mobile terminal, and operates the control terminal to complete examination on the patient; finally, the technician enters the scanning room from the technicians' access door with the mobile terminal, tells the patient to go down the sickbed, adjusts the sickbed, and waits for next patient.

The method according to the present disclosure is described in detail below with a specific embodiment. It is to be noted that the embodiment of the present disclosure may be performed by a terminal operation apparatus or a terminal. The terminal is the mobile terminal or the control terminal in FIG. 6. The following embodiment is described by taking the mobile terminal as an execution subject.

Figure 8:
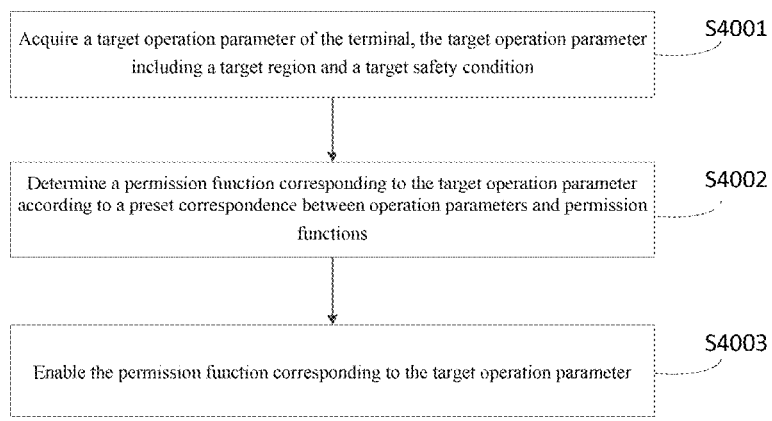
FIG. 8 is a schematic flowchart of a terminal operation method according to an embodiment.

In one embodiment, a terminal operation method is provided. This embodiment relates to a specific process of how the mobile terminal enables a permission function according to a target operation parameter. As shown in FIG. 8, the method may include the following steps.

In S4001, a target operation parameter of the terminal is acquired, the target operation parameter including a target region and a target safety condition.

The terminal here refers to the mobile terminal. When a human body is examined, a region may be generally divided into a safety region and a non-safety region.

Specifically, when the human body is examined using a CT device, the mobile terminal may first obtain a region and a safety condition of the mobile terminal and take the region as the target region. The safety condition serves as the target safety condition, and the target region and the target safety condition are used as the target operation parameter.

In S4002, a permission function corresponding to the target operation parameter is determined according to a preset correspondence between operation parameters and permission functions.

Figure 8A:
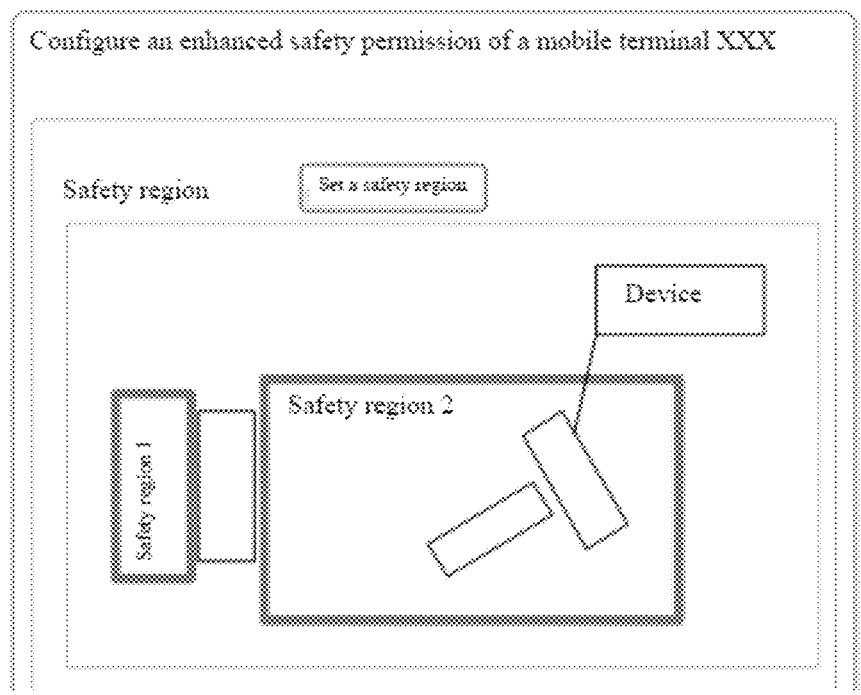
FIG. 8a is a schematic diagram of configuration of a safety region and a safety condition in the terminal operation method according to an embodiment.

Prior to the examination on the human body, the mobile terminal may first configure the safety region, the non-safety region and the safety condition; after the safety region and the safety condition are configured, the mobile terminal may continuously configure a correspondence between operation parameters (i.e., the safety region and the safety condition) and permission functions, that is, set different permission functions for different operation parameters, and enable the two to correspond to each other. The mobile terminal may configure the correspondence on its display interface or configure the correspondence on the control terminal. After the configuration, the control terminal is associated with the mobile terminal, and the mobile terminal can use the configured correspondence. In an example, a manner in which the mobile terminal configures the safety region and the safety condition may be obtained with reference to FIG. 8*a*.

Specifically, after obtaining the target operation parameter, the mobile terminal may search the pre-configured correspondence for the permission function corresponding to the target operation parameter.

In an example, as shown in FIG. 8*b*, different corresponding permission functions under different safety conditions when the mobile terminal is in different target regions are shown, from which it can be seen that different operation parameters correspond to different permission functions.

In S4003, the permission function corresponding to the target operation parameter is enabled.

specifically, after obtaining the permission function corresponding to the target operation parameter, the mobile terminal can enable the permission function. In this way, when examining a human body, the technician can control the sickbed to move or control the CT device to scan the human body by operating the enabled permission function.

According to the terminal operation method, a target operation parameter of a terminal is acquired, the target operation parameter includes a target region and a target safety condition, a permission function corresponding to the target operation parameter is determined according to a preset correspondence between operation parameters and permission functions, and the permission function corresponding to the target operation parameter is enabled. In this embodiment, the enabled permission function is determined according to two parameters, i.e., the target region and the target safety condition, that is, different target regions and target safety conditions correspond to different permission functions; in this way, when a human body is examined, all the functions may not be blindly used for examination, and only the permission function corresponding to the target operation parameter is enabled. Therefore, the method can enhance safety of the terminal. At the same time, when a CT device is operated using the terminal, safety of the CT device may also be enhanced, thereby reducing occurrence of some unexpected risks.

In another embodiment, this embodiment relates to a specific process of how the mobile terminal acquires the target operation parameter. On the basis of the above embodiment, as shown in FIG. 9, the method may include the following steps.

In S5001, a current position of the terminal and a current state of the terminal are acquired.

Figure 9A:
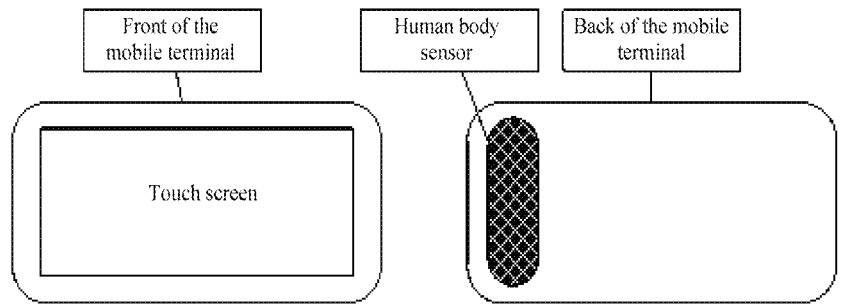
FIG. 9a is a schematic setting diagram of a human body sensor in the terminal operation method according to another embodiment.

The current state of the terminal refers to a current state of the mobile terminal. The state may include any one of being held, detached, and placed in a bracket. The "held" means that the technician holds the mobile terminal, the "placed in a bracket" means that the mobile terminal is attached to a rack of the CT device or the mobile terminal is placed in a bracket next to the control terminal, and the "detached" means that the mobile terminal is neither held by the technician nor placed in the bracket, that is, placed elsewhere. Optionally, as shown in FIG. 9*a*, a human body sensor may be arranged at the back of the mobile terminal, and whether the mobile terminal is hand-held (for example, whether induced capacitance changes) may be known by using a signal acquired by the human body sensor. Optionally, a charging apparatus may be arranged in the rack of the CT device or the bracket next to the control terminal. Whether the mobile terminal is placed in the bracket can be known according to whether the charging apparatus performs charging. The current position of the terminal refers to a current position of the mobile terminal. Generally, a plurality of Bluetooth beacons may be arranged in the operation room and the scanning room, and each Bluetooth beacon may be communicatively connected to the mobile terminal.

In addition, the current state of the terminal may further include: a current operation state of the CT device, for example, when the CT device sets scanning parameters, performs scanning, performs correction, reconstructs an image, and so on. When the mobile terminal obtains the safety condition, the target safety condition can be obtained by comprehensively considering the current state of the mobile terminal and the current operation state of the CT device. Different states may correspond to different safety conditions. By comprehensively considering current states of various devices, the safety conditions set can be more comprehensive, so that the operational safety of the mobile terminal is higher.

Specifically, the mobile terminal can calculate the current position of the mobile terminal through signal strength of each Bluetooth beacon received. Certainly, the current position of the mobile terminal may also be obtained through a positioning apparatus such as a GPS built in the mobile terminal. At the same time, the mobile terminal may obtain the current state of the mobile terminal through the signal acquired by the human body sensor and whether the charging apparatus performs charging. In an example, if the signal acquired by the human body sensor changes, it can be considered that the current state of the mobile terminal is "hand-held", or if the charging apparatus is performing charging, it can be considered that the current state of the mobile terminal is "placed in the bracket", and in other cases, it can be considered that the current state of the mobile terminal is "detached". For example, the mobile terminal is placed on a desktop. In addition, when the current state of the mobile terminal is "detached", optionally, a screen lock time can be set, such as 3 s. The mobile terminal may automatically lock a screen after being detached for 3 s, and a user can continue to use it only after re-authentication.

In S5002, the target region where the terminal is located is determined according to the current position of the terminal, and the target safety condition corresponding to the terminal is determined according to the current state of the terminal.

The safety condition is all the states of the mobile terminal, including hand-held, detached, placed in the bracket, and so on. A position of the safety region may also be obtained through the signal strength of each Bluetooth beacon.

Specifically, after obtaining its current position, the mobile terminal may match its current position with the position of the safety region, so as to obtain a region corresponding to the current position, which may be a safety region or a non-safety region. The region corresponding to the current position is recorded as the target region. In addition, the mobile terminal can obtain a state corresponding to the mobile terminal through the human body sensor and the charging apparatus. The corresponding state is recorded as the target safety condition.

In S5003, the target region and the target safety condition are used as the target operation parameter.

Specifically, the mobile terminal can combine the target region and the target safety condition as the target operation parameter after obtaining the target region and the target safety condition.

In the terminal operation method according to this embodiment, the current position of the terminal and the current state of the terminal are acquired, a target region where the terminal is located is determined according to the current position of the terminal, a target safety condition corresponding to the terminal is determined according to the current state of the terminal, and the target region and the target safety condition are used as the target operation parameter. In this embodiment, the target operation parameter is determined according to the current position and the current state of the terminal (i.e., the mobile terminal); that is, the target operation parameter is determined according to an actual position and an actual state of the mobile terminal. Therefore, when the permission function is enabled using the target operation parameter, the enabled permission function is also a permission function in line with reality, that is, a permission function that can be operated safely. Thus, the method can further improve the operational safety of the mobile terminal.

Figure 10:
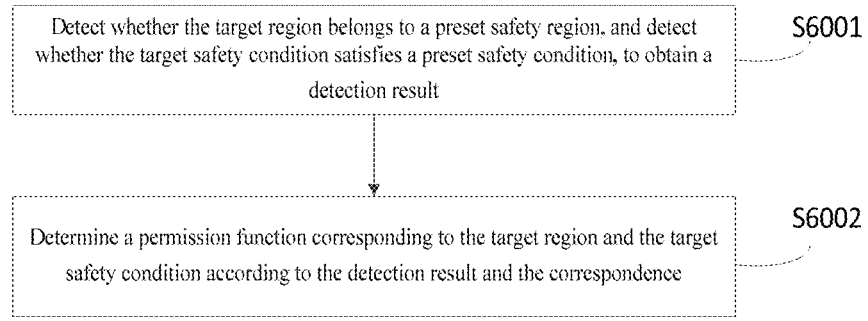
FIG. 10 is a schematic flowchart of a terminal operation method according to another embodiment.

In another embodiment, another terminal operation method is provided. This embodiment relates to a specific process of how the mobile terminal determines a corresponding permission function according to a target operation parameter and a preset correspondence between operation parameters and permission functions. On the basis of the above embodiment, as shown in FIG. 10, the method may include the following steps.

In S6001, it is detected whether the target region belongs to a preset safety region, and it is detected whether the target safety condition satisfies a preset safety condition, to obtain a detection result.

Figure 10A:
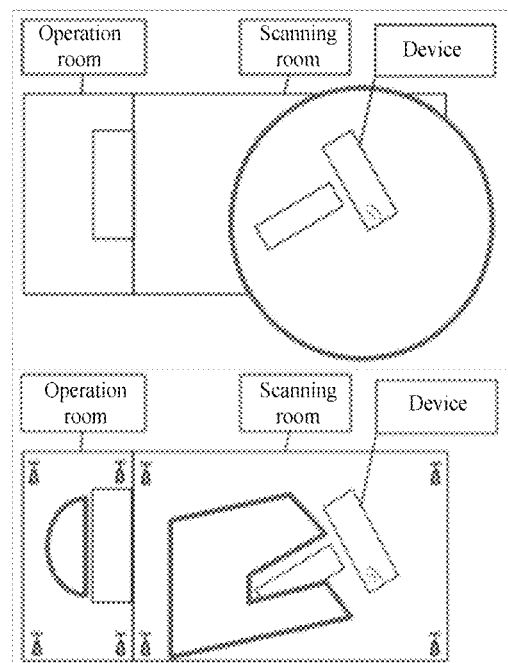
FIG. 10a is a schematic diagram of a shape of a safety region set in the terminal operation method according to an embodiment.

One or two or other numbers of preset safety regions may be provided. Two safety regions are provided in this embodiment, of which one is an operation room and the other is a scanning room. The safety region may be in a shape of a circle or a rectangle or other regular or irregular polygons. The circular safety region can generally be established with the WIFI routing component of the CT device as a center and with a specific length as a radius. For example, the set shape of the safety region is shown in FIG. 10a.

Specifically, the mobile terminal, after obtaining the target region and the target safety condition of the terminal, can detect whether the target region belongs to a preset safety region, to obtain the detection result; that is, the target region is matched with the preset safety region, if the match is successful, it indicates that the target region belongs to the preset safety region, and otherwise, it indicates that the region does not belong to the preset safety region but belongs to the non-safety region. In addition, the mobile terminal may also detect whether the target safety condition satisfies the preset safety condition, to obtain the detection result; that is, the target safety condition may be matched with the preset safety condition, if the match is successful, it indicates that the target safety condition belongs to the preset safety condition, and otherwise, the target safety condition does not belong to the preset safety condition.

In S6002, a permission function corresponding to the target region and the target safety condition is determined according to the detection result and the correspondence.

Specifically, the mobile terminal may obtain a plurality of detection results when detecting the target region and the target safety condition. The plurality of detection results may also correspond to a variety of different permission functions. The plurality of detection results may be as follows.

Optionally, it is determined, according to the correspondence, that the permission function corresponding to the target region and the target safety condition is all functions of the terminal when the detection result is that the target region belongs to the preset safety region and the target safety condition satisfies the preset safety condition. That is, when detecting that the target region belongs to the preset safety region and the target safety condition satisfies the preset safety condition, the mobile terminal can enable all the functions, and scan and examine the human body by using all the functions.

Optionally, all the functions of the terminal are disabled when the detection result is that the target region does not belong to the preset safety region and the target safety condition does not satisfy the preset safety condition. That is, when the mobile terminal detects that the target region does not belong to the preset safety region and the target safety condition does not satisfy the preset safety condition, it is determined that the mobile terminal may be in the non-safety region and in a non-safety state, and the mobile terminal is required to disable all the functions and cannot scan and examine the human body at will.

Optionally, it is determined, according to the correspondence, that the permission function corresponding to the target region is some functions of the terminal when the detection result is that the target region belongs to the preset safety region and the target safety condition does not satisfy the preset safety condition; or it is determined, according to the correspondence, that the permission function corresponding to the target safety condition is some functions of the terminal when the detection result is that the target region does not belong to the preset safety region and the target safety condition satisfies the preset safety condition. In this step, some functions corresponding to the case of belonging to the safety region and not satisfying the safety condition and some functions corresponding to the case of not belonging to the safety region and satisfying the safety condition may be the same or different. The terminal may enable some functions when the obtained detection result is such two cases. The mobile terminal may enable some functions; that is, the mobile terminal may perform corresponding operations on the human body by using the some functions. The some functions may include or not include a scanning operation.

Optionally, the mobile terminal may acquire a latest current position and a latest current state in real time (at any time), and when the target region of the current position and the safety condition that the current state satisfies change, may update the corresponding permission function in real time and perform corresponding processing.

In the terminal operation method according to this embodiment, a detection result is obtained by detecting whether the target region belongs to the preset safety region and detecting whether the target safety condition satisfies the preset safety condition, and a permission function corresponding to the target region and the target safety condition is determined according to the detection result and the correspondence. In this embodiment, permission functions corresponding to the mobile terminal may also be different under different detection results; that is, permission functions used by the mobile terminal in different scenarios are different. Therefore, the method can enhance the safety of the mobile terminal.

Figure 11:
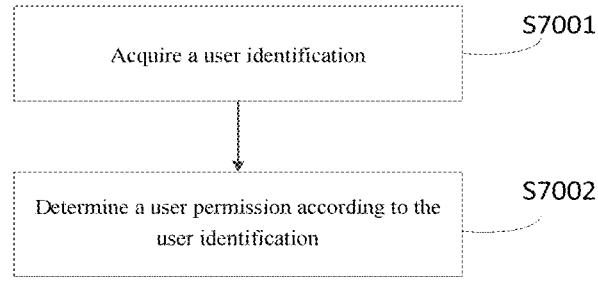
FIG. 11 is a schematic flowchart of a terminal operation method according to another embodiment.

In another embodiment, another terminal operation method is provided. This embodiment relates to a specific process of how the mobile terminal determines a user permission according to a user identification. On the basis of the above embodiment, as shown in FIG. 11, the method may further include the following steps.

In S7001, a user identification is acquired.

The user identification may be a user password, a user mobile communication number, a user ID number, a user communication software number, or the like.

Specifically, when a user is to log in the mobile terminal, a user identification can be entered on a login interface of the mobile terminal, so that the mobile terminal can obtain the user identification entered by the user.

In S7002, a user permission is determined according to the user identification.

Specifically, the mobile terminal, after obtaining the user identification entered by the user, may match the entered user identification with a preset user identification. When the match is successful, it can be determined that the user corresponding to the user identification logs in successfully, and the mobile terminal can be used.

In the terminal operation method according to this embodiment, a user identification is acquired, and a user permission is determined according to the user identification. In this embodiment, the user permission is determined according to the user identification, and this can avoid the problem of damages to the mobile terminal caused by arbitrary use of the mobile terminal by some people without the user permission. Therefore, the method can improve the safety of the mobile terminal.

Figure 12:
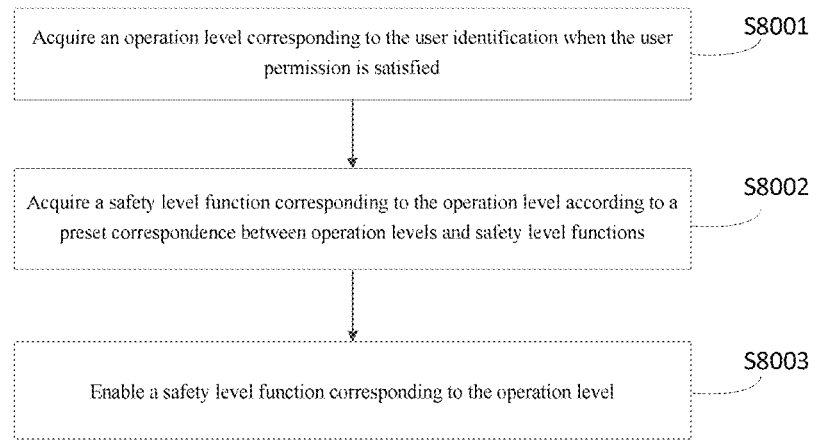
FIG. 12 is a schematic flowchart of a terminal operation method according to another embodiment.

In another embodiment, another terminal operation method is provided. This embodiment relates to a specific process of how the mobile terminal enables a safety level function corresponding to the user identification when the user permission is satisfied. On the basis of the above embodiment, as shown in FIG. 12, the method may further include the following steps.

In S8001, an operation level corresponding to the user identification is acquired when the user permission is satisfied.

Prior to the use of the mobile terminal, different operation levels may be preset for different user identifications; that is, a correspondence between user identifications and operation levels may be established. In an example, an operation level corresponding to a first user identification is 1, an operation level corresponding to a second user identification is 2, and so on.

Specifically, when the mobile terminal obtains that the user identification entered by the user satisfies the user permission, an operation level corresponding to the user identification can be obtain obtained from a preset mapping relationship between user identifications and operation levels.

In S8002, a safety level function corresponding to the operation level is acquired according to a preset correspondence between operation levels and safety level functions.

After setting different operation levels for different user identifications, the mobile terminal may also set a corresponding safety level function for each operation level, that is, set different safety level functions for different operation levels, and establish a correspondence between the operation levels and the safety level functions. In an example, the safety level function corresponding to the operation level 1 may be "bed-movement enabled", the safety level function corresponding to the operation level 2 may be "bed-movement enabled; scanning enabled", and so on.

Specifically, after obtaining the operation level corresponding to the user identification, the mobile terminal may also obtain a safety level function corresponding to the operation level according to a correspondence between operation levels and safety level functions.

In S8003, the safety level function corresponding to the operation level is enabled.

Specifically, the mobile terminal, after obtaining the safety level function corresponding to the operation level, can enable the function.

In the terminal operation method according to this embodiment, when a user permission is satisfied, an operation level corresponding to a user identification can be acquired, a safety level function corresponding to the operation level is acquired according to a preset correspondence between operation levels and safety level functions, and the safety level function corresponding to the operation level is enabled. In this embodiment, since different user identifications correspond to different operation levels, that is, correspond to different safety level functions, this can also further avoid an accident caused by misoperation of some users on functions that are not operable, thereby improving the safety of the mobile terminal.

It should be understood that although steps in the flowcharts of FIG. 8 to FIG. 12 are displayed in sequence as indicated by the arrows, the steps are not necessarily performed in sequence in the order indicated by the arrows. Unless otherwise clearly specified herein, the steps are performed without any strict sequence limitation, and may be performed in other orders. In addition, at least some steps in FIG. 8 to FIG. 12 may include a plurality of sub-steps or a plurality of stages, and these sub-steps or stages are not necessarily performed at a same moment, and may be performed at different moments. The sub-steps or stages are not necessarily performed in sequence, and the sub-steps or stages and at least some of other steps or sub-steps or stages of other steps may be performed in turn or alternately.

Figure 13:
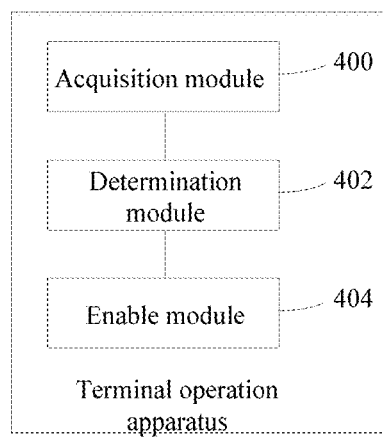
FIG. 13 is a structural block diagram of a terminal operation apparatus according to an embodiment.

In one embodiment, as shown in FIG. 13, a terminal operation apparatus is provided, including: an acquisition module 400, a determination module 402 and an enable module 404.

The acquisition module 400 is configured to acquire a target operation parameter of the terminal, the target operation parameter including a target region and a target safety condition.

The determination module 402 is configured to determine a permission function corresponding to the target operation parameter according to a preset correspondence between operation parameters and permission functions.

The enable module 404 is configured to enable the permission function corresponding to the target operation parameter.

The terminal operation apparatus according to the embodiment of the present disclosure can perform the above method embodiment. Their implementation principles and technical effects are similar, which are not described in detail herein.

In another embodiment, the acquisition module 400 is specifically configured to acquire a current position of the terminal and a current state of the terminal; determine, according to the current position of the terminal, the target region where the terminal is located, and determine, according to the current state of the terminal, the target safety condition corresponding to the terminal; and use the target region and the target safety condition as the target operation parameter.

In another embodiment, another terminal operation apparatus is provided. On the basis of the above embodiment, the determination module 402 may include: a detection unit and a determination unit.

The detection unit is configured to detect whether the target region belongs to a preset safety region, and detect whether the target safety condition satisfies a preset safety condition, to obtain a detection result.

The determination unit is configured to determine a permission function corresponding to the target region and the target safety condition according to the detection result and the correspondence.

In another embodiment, the determination unit is specifically configured to determine, according to the correspondence, that the permission function corresponding to the target region and the target safety condition is all functions of the terminal when the detection result is that the target region belongs to the preset safety region and the target safety condition satisfies the preset safety condition.

In another embodiment, the determination unit is further configured to disable all the functions of the terminal when the detection result is that the target region does not belong to the preset safety region and the target safety condition does not satisfy the preset safety condition.

In another embodiment, the determination unit is further configured to determine, according to the correspondence, that the permission function corresponding to the target region is some functions of the terminal when the detection result is that the target region belongs to the preset safety region and the target safety condition does not satisfy the preset safety condition; or determine, according to the correspondence, that the permission function corresponding to the target safety condition is some functions of the terminal when the detection result is that the target region does not belong to the preset safety region and the target safety condition satisfies the preset safety condition.

Figure 14:
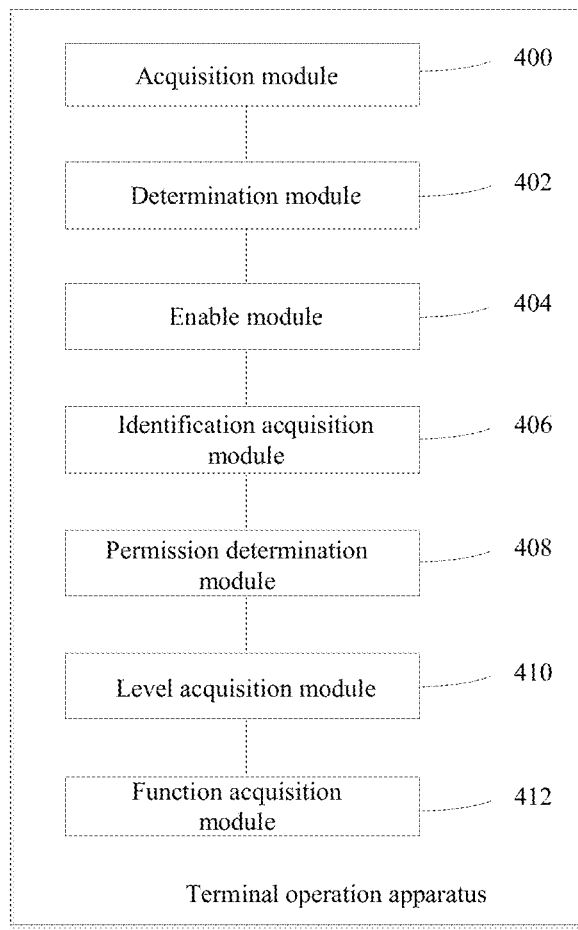
FIG. 14 is a structural block diagram of a terminal operation apparatus according to another embodiment.

In another embodiment, another terminal operation apparatus is provided. As shown in FIG. 14, on the basis of the above embodiment, the apparatus may further include: an identification acquisition module 406 and a permission determination module 408.

The identification acquisition module 406 is configured to acquire a user identification.

The permission determination module 408 is configured to determine a user permission according to the user identification.

In another embodiment, another terminal operation apparatus is provided. Still referring to FIG. 14, on the basis of the above embodiment, the apparatus may further include: a level acquisition module 410 and a function acquisition module 412.

The level acquisition module 410 is configured to acquire an operation level corresponding to the user identification when the user permission is satisfied.

The function acquisition module 412 is configured to acquire a safety level function corresponding to the operation level according to a preset correspondence between operation levels and safety level functions; and enable a safety level function corresponding to the operation level.

The terminal operation apparatus according to the embodiment of the present disclosure can perform the above method embodiment. Their implementation principles and technical effects are similar, which are not described in detail herein.

Figure 15:
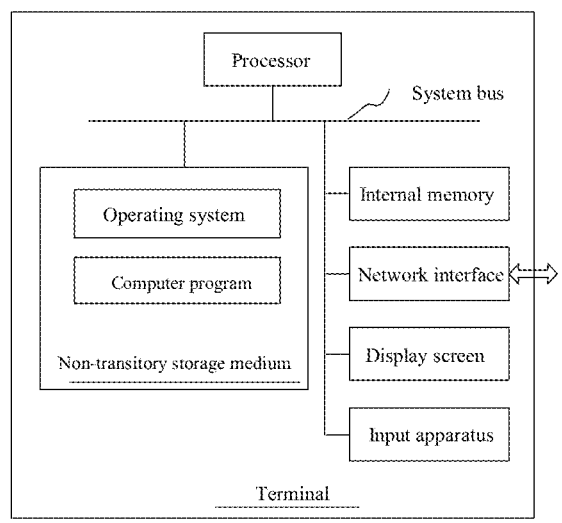
FIG. 15 is an internal structural diagram of a terminal according to an embodiment.

In one embodiment, a terminal is provided. The terminal may be a mobile terminal, and its internal structure diagram is shown in FIG. 15. The terminal includes a processor, a memory, a network interface, a display screen and an input apparatus that are connected through a system bus. The processor of the terminal is configured to provide computing and control capabilities. The memory of the terminal includes a non-transitory storage medium and an internal memory. The non-transitory storage medium stores an operating system and a computer program. The internal memory provides an environment for running of the operating system and the computer program in the non-transitory storage medium. The network interface of the terminal is configured to communicate with an external terminal through a network connection. The computer program performs a terminal operation method when executed by the processor. The display screen of the terminal may be a liquid crystal display screen or an electronic ink display screen. The input apparatus of the terminal may be a touch layer covering the display screen, or may be a key, a trackball, or a touchpad disposed on a housing of the terminal, or may be an external keyboard, a touchpad, a mouse, or the like.

Those skilled in the art may understand that a structure shown in FIG. 15 is only a block diagram of some structures related to the solution of the present disclosure and constitutes no limitation on the terminal to which the solution of the present disclosure is applied. Specifically, the terminal may include more or fewer components than those shown in the drawing, or some components may be combined, or a different component deployment may be used.

In one embodiment, a terminal is provided, including a memory and a processor. The memory stores a computer program, and the processor, when executing the computer program, performs the following steps:

acquiring a target operation parameter of a terminal, the target operation parameter including a target region and a target safety condition;

determining a permission function corresponding to the target operation parameter according to a preset correspondence between operation parameters and permission functions; and enabling the permission function corresponding to the target operation parameter.

In one embodiment, the processor, when executing the computer program, further performs the following steps:

acquiring a current position of the terminal and a current state of the terminal; determining, according to the current position of the terminal, the target region where the terminal is located, and determining, according to the current state of the terminal, the target safety condition corresponding to the terminal; and using the target region and the target safety condition as the target operation parameter.

In one embodiment, the processor, when executing the computer program, further performs the following steps:

detecting whether the target region belongs to a preset safety region, and detecting whether the target safety condition satisfies a preset safety condition, to obtain a detection result; and determining a permission function corresponding to the target region and the target safety condition according to the detection result and the correspondence.

In one embodiment, the processor, when executing the computer program, further performs the following steps:

determining, according to the correspondence, that the permission function corresponding to the target region and the target safety condition is all functions of the terminal when the detection result is that the target region belongs to the preset safety region and the target safety condition satisfies the preset safety condition.

In one embodiment, the processor, when executing the computer program, further performs the following steps:

disabling all the functions of the terminal when the detection result is that the target region does not belong to the preset safety region and the target safety condition does not satisfy the preset safety condition.

In one embodiment, the processor, when executing the computer program, further performs the following steps:

It is determined, according to the correspondence, that the permission function corresponding to the target region is some functions of the terminal when the detection result is that the target region belongs to the preset safety region and the target safety condition does not satisfy the preset safety condition; or it is determined, according to the correspondence, that the permission function corresponding to the target safety condition is some functions of the terminal when the detection result is that the target region does not belong to the preset safety region and the target safety condition satisfies the preset safety condition.

In one embodiment, the processor, when executing the computer program, further performs the following steps:

acquiring a user identification; and determining a user permission according to the user identification.

In one embodiment, the processor, when executing the computer program, further performs the following steps:

acquiring an operation level corresponding to the user identification when the user permission is satisfied; acquiring a safety level function corresponding to the operation level according to a preset correspondence between operation levels and safety level functions; and enabling the safety level function corresponding to the operation level.

In one embodiment, a readable storage medium is provided, having a computer program stored thereon. The computer program, when executed by a processor, performs the following steps:

acquiring a target operation parameter of a terminal, the target operation parameter including a target region and a target safety condition;

determining a permission function corresponding to the target operation parameter according to a preset correspondence between operation parameters and permission functions; and enabling the permission function corresponding to the target operation parameter.

In one embodiment, the computer program, when executed by the processor, further performs the following steps:

acquiring a current position of the terminal and a current state of the terminal; determining, according to the current position of the terminal, the target region where the terminal is located, and determining, according to the current state of the terminal, the target safety condition corresponding to the terminal; and using the target region and the target safety condition as the target operation parameter.

In one embodiment, the computer program, when executed by the processor, further performs the following steps:

detecting whether the target region belongs to a preset safety region, and detecting whether the target safety condition satisfies a preset safety condition, to obtain a detection result; and determining a permission function corresponding to the target region and the target safety condition according to the detection result and the correspondence.

In one embodiment, the computer program, when executed by the processor, further performs the following steps:

determining, according to the correspondence, that the permission function corresponding to the target region and the target safety condition is all functions of the terminal when the detection result is that the target region belongs to the preset safety region and the target safety condition satisfies the preset safety condition.

In one embodiment, the computer program, when executed by the processor, further performs the following steps:

disabling all the functions of the terminal when the detection result is that the target region does not belong to the preset safety region and the target safety condition does not satisfy the preset safety condition.

In one embodiment, the computer program, when executed by the processor, further performs the following steps:

It is determined, according to the correspondence, that the permission function corresponding to the target region is some functions of the terminal when the detection result is that the target region belongs to the preset safety region and the target safety condition does not satisfy the preset safety condition; or it is determined, according to the correspondence, that the permission function corresponding to the target safety condition is some functions of the terminal when the detection result is that the target region does not belong to the preset safety region and the target safety condition satisfies the preset safety condition.

In one embodiment, the computer program, when executed by the processor, further performs the following steps:

acquiring a user identification; and determining a user permission according to the user identification.

In one embodiment, the computer program, when executed by the processor, further performs the following steps:

acquiring an operation level corresponding to the user identification when the user permission is satisfied; acquiring a safety level function corresponding to the operation level according to a preset correspondence between operation levels and safety level functions; and enabling the safety level function corresponding to the operation level.

Those of ordinary skill in the art may understand that all or some procedures in the methods in the foregoing embodiments may be implemented by a computer-readable instruction instructing related hardware, the computer program may be stored in a non-transitory computer-readable storage medium, and when the computer program is executed, the procedures in the foregoing method embodiments may be implemented. Any reference to a memory, a storage, a database, or other media used in the embodiments according to the present disclosure may include a non-transitory and/or transitory memory. The non-transitory memory may include a read-only memory (ROM), a programmable ROM (PROM), an electrically programmable ROM (EPROM), an electrically erasable programmable ROM (EEPROM) or a flash memory. The transitory memory may include a random access memory (RAM) or an external high-speed cache memory. By way of illustration instead of limitation, the RAM is available in a variety of forms, such as a static RAM (SRAM), a dynamic RAM (DRAM), a synchronous DRAM (SDRAM), a dual data rate SDRAM (DDRSDRAM), an enhanced SDRAM (ESDRAM), a synchronization link (Synchlink) DRAM (SLDRAM), a memory Bus (Rambus) direct RAM (RDRAM), a direct memory bus dynamic RAM (DRDRAM), a memory bus dynamic RAM (RDRAM) and the like.

The technical features in the above embodiments may be randomly combined. For concise description, not all possible combinations of the technical features in the above embodiments are described. However, all the combinations of the technical features are to be considered as falling within the scope described in this specification provided that they do not conflict with each other.

With the rapid development of medical imaging devices (also known as medical devices), an increasing number of disease diagnoses rely on detection and analysis of medical images. In order to facilitate a doctor to operate a medical device to scan a patient, a mobile terminal communicatively connected to the medical device has been currently added to assist the scanning of the medical device. The doctor can use the mobile terminal to control a position of the sickbed, and then return to a console of the medical device to control the medical device to scan the patient.

Currently, when the doctor returns to a console with the mobile terminal, a display mode of an interface of the mobile terminal is still an operation interface for controlling the sickbed, or the mobile terminal is in a screen-off state when placed on a special charging base near the console. In this way, the mobile terminal has low utilization and poor interactivity.

Based on this, there is a need to provide a terminal mode switching method, apparatus, terminal, system and readable storage medium with respect to the problem of low utilization and poor interactivity of the mobile terminal in the conventional art.

Figure 16:
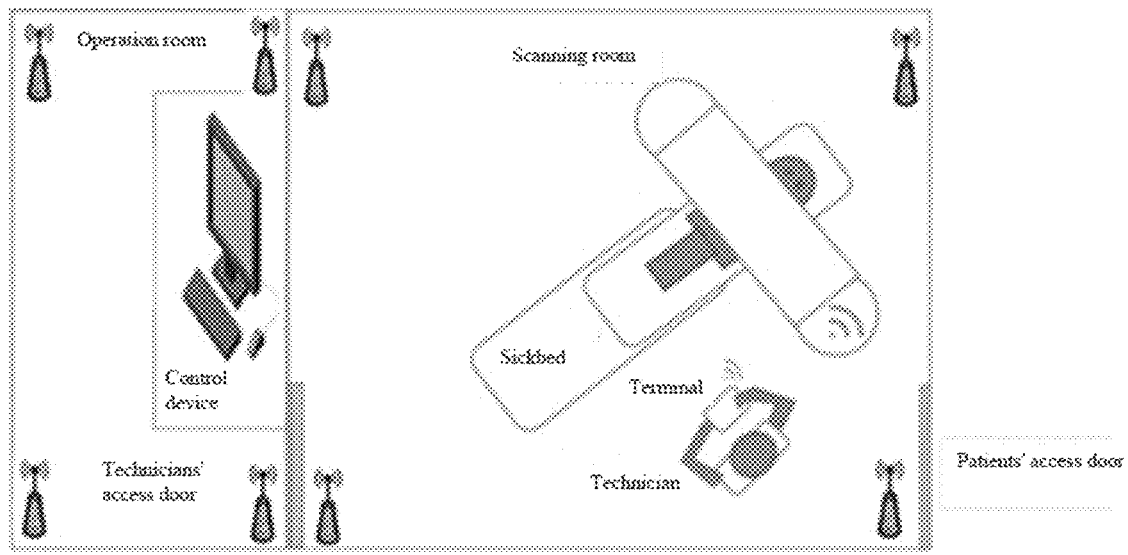
FIG. 16 is a schematic diagram of an application scenario of a terminal mode switching method according to an embodiment.

The terminal mode switching method according to the embodiment of the present disclosure can be applied to a scenario shown in FIG. 16. In a current working process of a medical device, firstly, a patient enters a scanning room from a patients' access door, and then follows a technician's instructions to lie on a sickbed; the technician holds a terminal, operates the terminal to control the sickbed to rise and advance, and positions a to-be-scanned site of the patient; then, the technician returns to the operation room from a technicians' access door with the terminal, and operates a control device to complete examination on the patient; finally, the technician enters the scanning room from the technicians' access door with the terminal, tells the patient to go down the sickbed, and waits for next patient. However, when the technician returns from the technician access door to the operation room with the terminal to operate the control device, the display mode of the interface of the terminal is still the operation interface for controlling the sickbed, or the terminal is in a screen-off state when placed on a special charging base near the control device. In this way, the terminal has low utilization and poor interactivity. The terminal mode switching method, apparatus, terminal, system and readable storage medium according to the embodiments of the present disclosure are intended to solve the above technical problem.

In order to make the objectives, technical solutions and advantages of the present disclosure clearer, the present disclosure is described in further detail below with reference to the accompanying drawings and embodiments. It should be understood that particular embodiments described herein are intended only to interpret the present disclosure and not intended to limit the present disclosure.

It is to be noted that the following method embodiment may be performed by a terminal mode switching apparatus. The apparatus may be implemented as part or all of a terminal by means of software, hardware, or a combination of hardware and software. The terminal may be the mobile terminal in the conventional art. For example, the following method embodiment is performed by a terminal.

Figure 17:
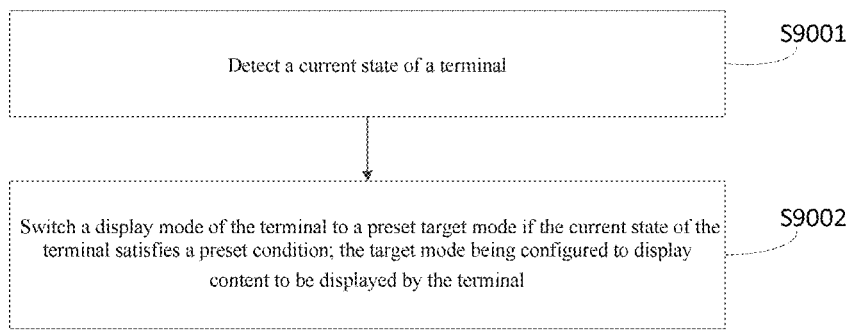
FIG. 17 is a schematic flowchart of a terminal mode switching method according to an embodiment.

FIG. 17 is a schematic flowchart of a terminal mode switching method according to an embodiment. This embodiment relates to a specific process of switching, by a terminal, a display mode to a target mode. As shown in FIG. 17, the method includes the following steps.

In S9001, a current state of a terminal is detected.

Specifically, the terminal first detects its current state. The terminal may be a mobile terminal communicatively connected to a control device. The control device may be a device that controls a medical device to scan a subject to obtain a medical image. The current state may be a current operation state or position state of the terminal. The operation state may be a state of controlling the sickbed, a state of communicating with the control device or a charged state. The position state may be a state of being in the scanning room or a state of being in the operation room. Optionally, the position state of the terminal may also be obtained from the operation state thereof. For example, when the position state of the terminal is the state of controlling the sickbed, it can be determined that the terminal is in the state of being in the scanning room; when the position state of the terminal is the state of communicating with the control device or the charged state, it can be determined that the terminal is in the state of being in the operation room.

In S9002, a display mode of the terminal is switched to a preset target mode if the current state of the terminal satisfies a preset condition; the target mode is configured to display content to be displayed by the terminal.

Specifically, the terminal may switch the display mode to the preset target mode when the current state detected by the terminal satisfies the preset condition. The preset condition may be a condition set for the operation state of the terminal or a condition set for the position state of the terminal. When the preset condition is the condition set for the position state of the terminal, if the terminal is in a state of being in the operation room, it is considered that the preset condition is satisfied, and the display mode of the terminal is switched to a target mode. When the preset condition is the condition set for the operation state of the terminal, if the operation state of the terminal is in a state of being in communication with the control device or in the charged state, it is considered that the preset condition is satisfied, and the display mode of the terminal is switched to the target mode.

The target mode may be a display operation mode preset according to a user requirement, which is set to, such as, display operation guidelines for operating the control device, display device parameters of the medical device, display physical sign information of the subject, or display content of a monitor in the scanning room. The target mode is configured to display content to be displayed by the terminal, but specific display content is not limited in this embodiment. Certainly, the target mode may also be configured to indicate other operation modes of the terminal, for example, a video recording mode, in which a process of the technician operating the control device currently is recorded for a new technician to learn.

After the terminal is switched to the target mode, a scanning process of the medical image may be extended from one screen of a conventional control device to two screens: one screen is an operation screen of the control device and the other screen is a display screen of the terminal, which provides more convenience for the user to scan a medical image of a subject.

According to the terminal mode switching method, the terminal first detects a current state; and a display mode of the terminal is switched to a preset target mode if the current state satisfies a preset condition. The target mode is configured to display content to be displayed by the terminal. In the method, when a technician returns to an operation room with the terminal and no longer controls a sickbed, the terminal can automatically change the display mode to a target mode set as needed, which greatly improves the utilization of the terminal and also improves interactivity of the terminal in use.

Optionally, in some embodiments, the step of detecting a current state of a terminal includes: detecting whether the terminal receives a preset sensing signal, or whether the terminal is in a charged state, or position information of the terminal.

Optionally, the step of detecting whether the terminal receives a preset sensing signal may include: detecting whether the terminal receives a sensing signal sent by a sensor by Near Field Communication (NFC). The sensor may be installed on the control device and may emit a sensing signal over a certain distance. A coverage range of the sensing signal is a regional range of the operation room. It may be determined, by detecting whether the terminal receives the sensing signal, that the terminal enters the operation room. Optionally, a manner of detecting whether the terminal is in the charged state may include: detecting whether a battery current of the terminal exceeds a current threshold, and determining that the terminal is in the charged state if yes. A special charging base of the terminal is generally arranged near the console. It may be determined, by detecting whether the terminal is in the charged state, that the terminal enters the operation room. Optionally, the position information of the terminal may be obtained by a user input, obtained by identification of an image taken by a camera in the operation room, or by a signal from a positioner in the terminal. It may be determined, by detecting whether the position of the terminal is in a region of the operation room (i.e., target position), that the terminal enters the operation room.

Optionally, different modes may also be switched to according to current state information of the terminal. For example, when the terminal is in the operation room, an operation mode may be switched to and an operation interface is displayed. When the terminal is within a certain range of the medical device, it is considered that the user is placing the patient, a placement mode may be switched to, and a placement interface is displayed; specifically, a real-time video of the patient shot by a top camera in the operation room at this time, a pre-shot positioning video and a pre-set medical scanning target region can be displayed. When the terminal is located far away from the medical device, it is considered that the user is required to use the terminal to read the video, a video reading mode may be switched to, and a sequence of recently shot images is displayed first.

Optionally, in some embodiments, if the terminal receives the sensing signal or the terminal is in the charged state or the terminal is at the target position, it can be determined that the current state of the terminal satisfies a preset condition; that is, the terminal enters the operation room at this time, and its display mode can be switched to the target mode. This setting can ensure that when the technician returns to the operation room to scan the subject, the terminal switches the display mode instead of displaying the mode of controlling the sickbed, which improves the utilization of the terminal, also improves the safety of the subject during the scanning, and avoids safety accident caused by misoperation of the technician on the terminal.

Optionally, in some embodiments, the content to be displayed by the terminal is preset content stored in the terminal, for example, operation guidelines for operating the control device. The preset content is pre-stored in the terminal. After the terminal switches to the target mode, the preset content is automatically displayed in the target mode. Thus, power consumption of communication between the terminal and the control device is reduced, and the operation complexity of the terminal is reduced.

Figure 18:
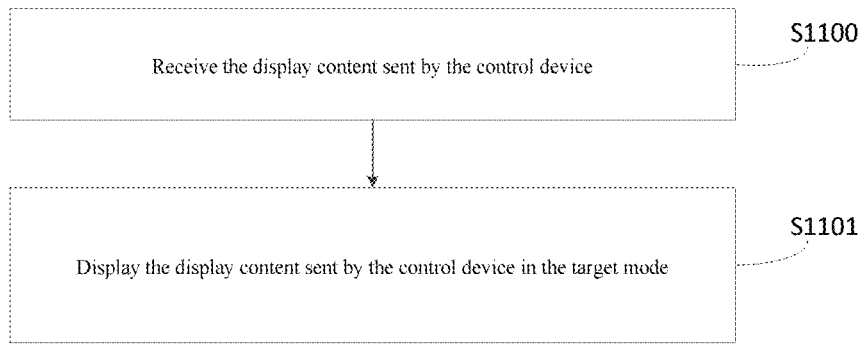
FIG. 18 is a schematic flowchart of a terminal mode switching method according to another embodiment.

Optionally, in some embodiments, the content to be displayed by the terminal is a display content sent by a control device, for example, device parameters of the medical device or displayed physical sign information of a subject. The display content sent by the control device may be sent according to an input instruction of the technician; that is, the control device can send the display content to the terminal according to a user requirement. As shown in FIG. 18, after the terminal switches to the target mode, the method further includes the following steps.

In S1100, the display content sent by the control device is received.

In S1101, the display content sent by the control device is displayed in the target mode.

Specifically, the communication connection between the terminal and the control device may be a wireless communication connection or a wired communication connection. In the case of the wired communication connection, the technician may connect a connecting line with the terminal when the terminal is in the operation room. In the case of the wireless communication connection, wireless data communication may be radio frequency transmission, Bluetooth signal transmission, or the like. The terminal, after receiving the display content sent by the control device, may display the display content in the target mode.

In the terminal mode switching method according to this embodiment, a terminal may receive display content sent by a control device, and displays the display content sent by the control device in a target mode. Thus, the user can enable the terminal to display the corresponding display content as needed, which further improves the utilization of the terminal as well as interaction between users.

It should be understood that although steps in the flowcharts of FIG. 17 and FIG. 18 are displayed in sequence as indicated by the arrows, the steps are not necessarily performed in sequence in the order indicated by the arrows. Unless otherwise clearly specified herein, the steps are performed without any strict sequence limitation, and may be performed in other orders. In addition, at least some steps in FIG. 17 and FIG. 18 may include a plurality of sub-steps or a plurality of stages, and these sub-steps or stages are not necessarily performed at a same moment, and may be performed at different moments. The sub-steps or stages are not necessarily performed in sequence, and the sub-steps or stages and at least some of other steps or sub-steps or stages of other steps may be performed in turn or alternately.

Figure 19:
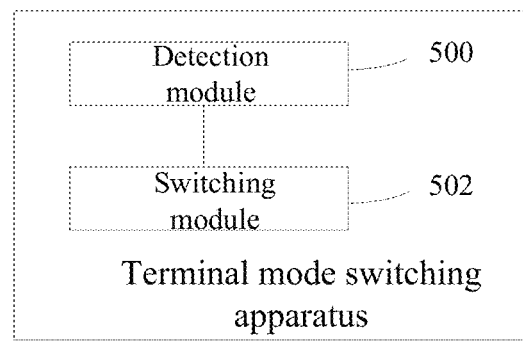
FIG. 19 is a schematic structural diagram of a terminal mode switching apparatus according to an embodiment.

FIG. 19 is a schematic structural diagram of a terminal mode switching apparatus according to an embodiment. As shown in FIG. 19, the apparatus includes: a detection module 500 and a switching module 502.

The detection module 500 is configured to detect a current state of a terminal.

The switching module 502 is configured to switch a display mode of the terminal to a preset target mode if the current state of the terminal satisfies a preset condition; the target mode being configured to display content to be displayed by the terminal.

The terminal operation apparatus according to this embodiment can perform the above method embodiment. Their implementation principles and technical effects are similar, which are not described in detail herein.

In one embodiment, the detection module 500 is specifically configured to determine whether the terminal receives a preset sensing signal, or whether the terminal is in a charged state, or position information of the terminal.

In one embodiment, the detection module 500 is specifically configured to detect whether the terminal receives a sensing signal sent by a sensor by near field communication.

In one embodiment, the switching module 502 is specifically configured to determine that the current state of the terminal satisfies the preset condition if the terminal receives the sensing signal, the terminal is in a charged state, or the terminal is at a target position.

Figure 20:
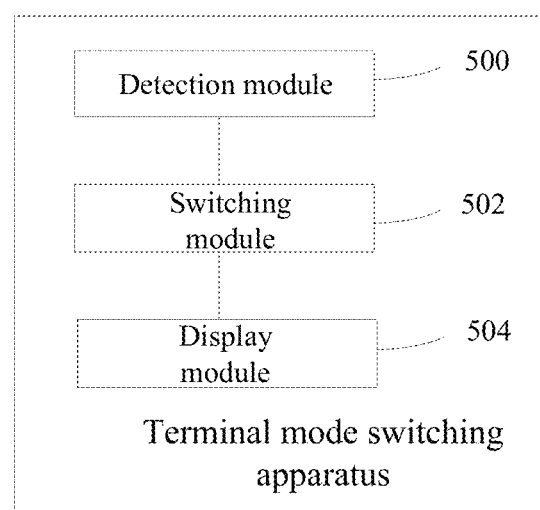
FIG. 20 is a schematic structural diagram of a terminal mode switching apparatus according to another embodiment.

In one embodiment, the content to be displayed by the terminal is preset content stored in the terminal; as shown in FIG. 20, the apparatus further includes: a display module 504 configured to display the preset content in the target mode.

In one embodiment, the content to be displayed by the terminal is a display content sent by a control device; the display module 504 is further configured to receive the display content sent by the control device and display the display content sent by the control device in the target mode.

Specific limitations on the terminal mode switching apparatus may be obtained with reference to the limitations on the terminal mode switching method described above, and are not described in detail herein. Each module in the above terminal mode switching apparatus may be entirely or partially implemented by using software, hardware, or a combination thereof. The above modules may be built in or independent of a processor of a computer device in a hardware form, or may be stored in a memory of the computer device in a software form, so that the processor invokes and performs an operation corresponding to each of the above modules.

Figure 21:
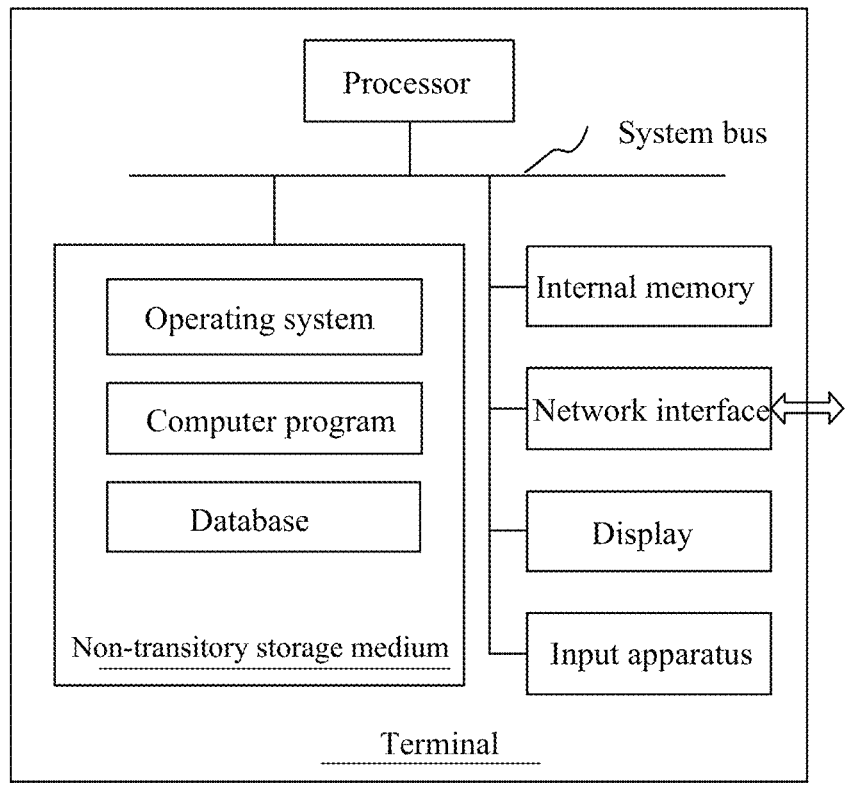
FIG. 21 is a schematic diagram of an internal structure of a terminal according to an embodiment.

In one embodiment, a terminal is provided. Its internal structure diagram is shown in FIG. 21. The terminal includes a processor, a memory, a network interface, a display and an input apparatus that are connected through a system bus. The processor of the terminal is configured to provide computing and control capabilities. The memory of the terminal includes a non-transitory storage medium and an internal memory. The non-transitory storage medium stores an operating system, a computer program and a database. The internal memory provides an environment for running of the operating system and the computer program in the non-transitory storage medium. The network interface of the terminal is configured to communicate with an external terminal through a network connection. The computer program performs a terminal mode switching method when executed by the processor. The display of the terminal may be a liquid crystal display screen or an electronic ink display screen. The input apparatus of the terminal may be a touchscreen covering the display screen, or may be a key, a trackball, or a touchpad disposed on a housing of the terminal, or may be an external keyboard, a touchpad, a mouse, or the like.

Those skilled in the art may understand that a structure shown in FIG. 21 is only a block diagram of some structures related to the solution of the present disclosure and constitutes no limitation on the terminal to which the solution of the present disclosure is applied. Specifically, the terminal may include more or fewer components than those shown in the drawing, or some components may be combined, or a different component deployment may be used.

In one embodiment, a terminal is provided, including a memory, a processor and a display. The memory stores a computer program. The processor, when executing the computer program, performs the following steps:

detecting a current state of a terminal; and switching a display mode of the terminal to a preset target mode if the current state of the terminal satisfies a preset condition; the target mode being configured to display content to be displayed by the terminal;

the display being configured to display content to be displayed by the terminal.

The implementation principle and technical effect of the terminal according to this embodiment are similar to those in the above method embodiment, and are not described in detail herein.

In one embodiment, the processor, when executing the computer program, further performs the following steps:

detecting whether the terminal receives a preset sensing signal, or whether the terminal is in a charged state, or position information of the terminal.

In one embodiment, the processor, when executing the computer program, further performs the following steps:

detecting whether the terminal receives a sensing signal sent by a sensor by near field communication.

In one embodiment, the processor, when executing the computer program, further performs the following steps:

determining that the current state of the terminal satisfies the preset condition if the terminal receives the sensing signal, the terminal is in a charged state, or the terminal is at a target position.

In one embodiment, the content to be displayed by the terminal is preset content stored in the terminal; and the processor, when executing the computer program, further performs the following step:

displaying the preset content in the target mode.

In one embodiment, the content to be displayed by the terminal is a display content sent by a control device; and the processor, when executing the computer program, further performs the following step:

receiving the display content sent by the control device; and displaying the display content sent by the control device in the target mode.

Figure 22:
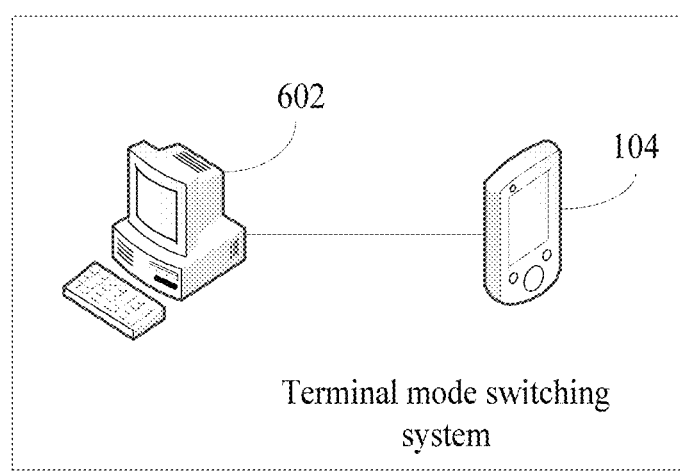
FIG. 22 is a schematic structural diagram of a terminal mode switching system according to an embodiment.

In one embodiment, as shown in FIG. 22, a terminal mode switching system is provided, including a terminal 104 and a control device 602. The terminal 104 is communicatively connected to the control device 602. The terminal 104 is configured to perform the following steps:

detecting a current state of the terminal 104; and switching a display mode of the terminal 104 to a preset target mode if the current state of the terminal 104 satisfies a preset condition; the target mode being configured to display content to be displayed by the terminal 104;

the control device 602 being configured to send display content to the terminal 104.

The implementation principle and technical effect of the terminal mode switching system according to this embodiment are similar to those in the above method embodiment, and are not described in detail herein.

In one embodiment, a readable storage medium is provided, having a computer program stored thereon. The computer program, when executed by a processor, performs the following steps:

detecting a current state of a terminal; and switching a display mode of the terminal to a preset target mode if the current state of the terminal satisfies a preset condition; the target mode being configured to display content to be displayed by the terminal.

The implementation principle and technical effect of the readable storage medium according to this embodiment are similar to those in the above method embodiment, and are not described in detail herein.

In one embodiment, the computer program, when executed by the processor, further performs the following steps:

detecting whether the terminal receives a preset sensing signal, or whether the terminal is in a charged state, or position information of the terminal.

In one embodiment, the computer program, when executed by the processor, further performs the following steps:

detecting whether the terminal receives a sensing signal sent by a sensor by near field communication.

In one embodiment, the computer program, when executed by the processor, further performs the following steps:

determining that the current state of the terminal satisfies the preset condition if the terminal receives the sensing signal, the terminal is in a charged state, or the terminal is at a target position.

In one embodiment, the content to be displayed by the terminal is preset content stored in the terminal; and the computer program, when executed by the processor, further performs the following step:

displaying the preset content in the target mode.

In one embodiment, the content to be displayed by the terminal is a display content sent by a control device; and the computer program, when executed by the processor, further performs the following steps:

receiving the display content sent by the control device; and displaying the display content sent by the control device in the target mode.

Those of ordinary skill in the art may understand that all or some procedures in the methods in the foregoing embodiments may be implemented by a computer-readable instruction instructing related hardware, the computer program may be stored in a non-transitory computer-readable storage medium, and when the computer program is executed, the procedures in the foregoing method embodiments may be implemented. Any reference to a memory, a storage, a database, or other media used in the embodiments according to the present disclosure may include a non-transitory and/or transitory memory. The non-transitory memory may include a read-only memory (ROM), a programmable ROM (PROM), an electrically programmable ROM (EPROM), an electrically erasable programmable ROM (EEPROM) or a flash memory. The transitory memory may include a random access memory (RAM) or an external high-speed cache memory. By way of illustration instead of limitation, the RAM is available in a variety of forms, such as a static RAM (SRAM), a dynamic RAM (DRAM), a synchronous DRAM (SDRAM), a dual data rate SDRAM (DDRSDRAM), an enhanced SDRAM (ESDRAM), a synchronization link (Synchlink) DRAM (SLDRAM), a memory Bus (Rambus) direct RAM (RDRAM), a direct memory bus dynamic RAM (DRDRAM), a memory bus dynamic RAM (RDRAM) and the like.

The technical features in the above embodiments may be randomly combined. For concise description, not all possible combinations of the technical features in the above embodiments are described. However, all the combinations of the technical features are to be considered as falling within the scope described in this specification provided that they do not conflict with each other.

The above embodiments only describe several implementations of the present disclosure, which are described specifically and in detail, and therefore cannot be construed as a limitation on the invention patent scope. It should be pointed out that those of ordinary skill in the art may also make several changes and improvements without departing from the ideas of the present disclosure, all of which fall within the protection scope of the present disclosure. Therefore, the patent protection scope of the present disclosure shall be subject to the appended claims.

What is claimed is:

1. A method for controlling a medical device, applied to a control system comprising an information detection apparatus, a device control apparatus and a terminal, the method comprising:

detecting, by the information detection apparatus, identification information of the terminal within a preset safety distance range, and sending the identification information to the device control apparatus;

determining, by the terminal, a current permission function of the terminal according to an acquired target operation parameter when the identification information has been verified by the device control apparatus, the target operation parameter comprising a target region where the terminal is currently located and a target safety condition;

receiving, by the device control apparatus, an operation instruction corresponding to the permission function and sent by the terminal, and controlling the medical device to perform an operation corresponding to the operation instruction; and switching, by the terminal, a display mode to a preset target mode when a current state of the terminal satisfies a preset condition, the target mode being configured to display content to be displayed by the terminal;

wherein the determining, by the terminal, the current permission function of the terminal according to the acquired target operation parameter comprises:

determining, by the terminal, the current permission function of the terminal according to the target operation parameter and a preset correspondence between operation parameters and permission functions;

wherein the determining, by the terminal, the current permission function of the terminal according to the target operation parameter and the preset correspondence between operation parameters and permission functions comprises:
detecting, by the terminal, whether the target region belongs to a preset safety region, and detecting whether the target safety condition satisfies a preset safety condition, to obtain a detection result; and
determining, by the terminal, the current permission function of the terminal according to the detection result and the correspondence.

2. The method according to claim 1, wherein the method further comprises:
verifying, by the device control apparatus, whether the identification information matches preset identification information, and indicating the identification information passes the verification if the identification information matches the preset identification information.

3. The method according to claim 2, wherein the step of detecting, by the information detection apparatus, identification information of the terminal within a preset safety distance comprises:
detecting, by the information detection apparatus, identification information of at least one terminal within the preset safety distance range, the preset safety distance range being 0 m to 3 m.

4. The method according to claim 3, wherein the step of matching, by the device control apparatus, the identification information with preset identification information for verification comprises:
acquiring, by the device control apparatus, a plurality of identification information sent by the information detection apparatus; and
verifying the plurality of identification information and the preset identification information one by one.

5. The method according to claim 1, wherein the method further comprises:
detecting, by the terminal, the current state; and the step of detecting, by the terminal, the current state comprises:
detecting, by the terminal, whether a preset sensing signal is received, or whether the terminal is in a charged state, or position information of the terminal.

6. The method according to claim 5, wherein a current state of the terminal satisfying a preset condition comprises:
determining that the current state of the terminal satisfies the preset condition if the terminal receives the sensing signal, the terminal is in a charged state, or the terminal is at a target position.

7. The method according to claim 6, wherein the content to be displayed by the terminal is preset content stored in the terminal; and after the step of switching, by the terminal, a display mode to a preset target mode, the method further comprises:
displaying the preset content in the target mode.

8. A terminal operation method, comprising:
acquiring a target operation parameter of the terminal, the target operation parameter comprising a target region and a target safety condition, the target region comprising a safety region and a non-safety region, and the target safety condition being determined by a current state of the terminal and a current operation state of a medical device;
determining a permission function corresponding to the target operation parameter according to a preset correspondence between operation parameters and permission functions; and
enabling the permission function corresponding to the target operation parameter.

9. The method according to claim 8, wherein the step of acquiring a target operation parameter of the terminal comprises:
acquiring a current position of the terminal and the current state of the terminal;
determining, according to the current position of the terminal, the target region where the terminal is located, and determining, according to the current state of the terminal, the target safety condition corresponding to the terminal; and
using the target region and the target safety condition as the target operation parameter.

10. The method according to claim 9, wherein the step of determining a permission function corresponding to the target operation parameter according to a preset correspondence between operation parameters and permission functions comprises:
detecting whether the target region belongs to a preset safety region, and detecting whether the target safety condition satisfies a preset safety condition, to obtain a detection result; and
determining a permission function corresponding to the target region and the target safety condition according to the detection result and the correspondence.

11. A terminal mode switching method, comprising:
detecting a current state of a terminal; and
switching a display mode of the terminal to a preset target mode if the current state of the terminal satisfies a preset condition, the target mode being configured to display content to be displayed by the terminal, and indicate operation modes of the terminal in addition to the display mode,
wherein the current state of the terminal comprises a current operation state and a position state of the terminal, the operation state comprises a state of controlling a sickbed, a state of communicating with a control device and a charged state, and the position state comprises a state of being in a scanning room and a state of being in an operation room.

12. The method according to claim 11, wherein the step of detecting a current state of a terminal comprises:
detecting whether the terminal receives a preset sensing signal, or whether the terminal is in a charged state, or position information of the terminal.

* * * * *